US012485221B2

(12) United States Patent
Lindo et al.

(10) Patent No.: US 12,485,221 B2
(45) **Date of Patent: *Dec. 2, 2025**

(54) INFUSION SYSTEM AND PUMP WITH CONFIGURABLE CLOSED LOOP DELIVERY RATE CATCH-UP

(71) Applicant: ICU Medical, Inc., San Clemente, CA (US)

(72) Inventors: Steve Joseph Lindo, Chicago, IL (US); William Kenneth Day, Hoffman Estates, IL (US)

(73) Assignee: ICU Medical, Inc., San Clemente, CA (US)

( * ) Notice: Subject to any disclaimer, the term of this patent is extended or adjusted under 35 U.S.C. 154(b) by 827 days.

This patent is subject to a terminal disclaimer.

(21) Appl. No.: 17/804,548

(22) Filed: May 27, 2022

(65) Prior Publication Data

US 2022/0362463 A1 Nov. 17, 2022

Related U.S. Application Data

(63) Continuation of application No. 14/725,077, filed on May 29, 2015, now Pat. No. 11,344,673.

(Continued)

(51) Int. Cl.
*A61M 5/168* (2006.01)
*A61M 5/172* (2006.01)

(52) U.S. Cl.
CPC ....... *A61M 5/16827* (2013.01); *A61M 5/1723* (2013.01)

(58) Field of Classification Search
None
See application file for complete search history.

(56) References Cited

U.S. PATENT DOCUMENTS 3,401,337 A 9/1968 Beusman et al.
3,484,681 A 12/1969 Grady, Jr. et al.

(Continued)

FOREIGN PATENT DOCUMENTS

AU 2013216679 9/2013
BR PI0704229-9 11/2009

(Continued)

OTHER PUBLICATIONS

Abbott Laboratories, "LifeCare® 5000, Plum®: Concurrent Flow Infusion System with DataPort™", System Operating Manual, Version 1.6, Jul. 1998, pp. 76.

(Continued)

*Primary Examiner* — Manuel A Mendez

(74) *Attorney, Agent, or Firm* — Knobbe, Martens, Olson & Bear, LLP

(57) ABSTRACT

An infusion system and pump with configurable closed loop delivery rate catch-up including an infusion system having a medication management unit and a medical device. The medication management unit has programming code to: provide a graphical user interface for modifying a drug library; receive a catch-up rate factor; update the drug library with the catch-up rate factor; and transmit the updated drug library to the medical device. The medical device has programming code to: receive the updated drug library; receive a desired infusion rate; calculate expected accumulated infusion volume from the desired infusion rate; request delivery of the infusion at the desired infusion rate; determine actual accumulated infusion volume at a particular time; increase the infusion rate by the catch-up rate factor to generate a catch-up infusion rate when at the particular time the actual accumulated infusion volume is less than expected; and request infusion at the catch-up infusion rate.

20 Claims, 12 Drawing Sheets

Related U.S. Application Data

(60) Provisional application No. 62/004,688, filed on May 29, 2014.

(56) References Cited

U.S. PATENT DOCUMENTS 3,699,320 A 10/1972 Zimmerman et al.
3,727,074 A 4/1973 Keller et al.
3,731,679 A 5/1973 Wilhelmson et al.
3,768,084 A 10/1973 Haynes
3,770,354 A 11/1973 Tsuruta et al.
3,778,702 A 12/1973 Finger
3,806,821 A 4/1974 Niemeyer et al.
3,838,565 A 10/1974 Carlyle
3,847,138 A 11/1974 Gollub
3,854,038 A 12/1974 McKinley
3,886,459 A 5/1975 Hufford et al.
3,890,554 A 6/1975 Yoshitake et al.
3,894,431 A 7/1975 Muston et al.
3,898,637 A 8/1975 Wolstenholme
3,901,231 A 8/1975 Olson
3,909,693 A 9/1975 Yoshitake et al.
3,910,701 A 10/1975 Henderson
3,911,343 A 10/1975 Oster
3,919,608 A 11/1975 Usami et al.
3,921,622 A 11/1975 Cole
3,930,404 A 1/1976 Ryden, Jr.
3,933,431 A 1/1976 Trujillo et al.
3,935,876 A 2/1976 Massie et al.
3,944,963 A 3/1976 Hively
3,966,358 A 6/1976 Heimes et al.
3,971,980 A 7/1976 Jungfer et al.
3,974,681 A 8/1976 Namery
3,974,683 A 8/1976 Martin
3,985,467 A 10/1976 Lefferson
3,990,444 A 11/1976 Vial
3,997,888 A 12/1976 Kremer
4,005,724 A 2/1977 Courtot
4,014,206 A 3/1977 Taylor
4,038,982 A 8/1977 Burke
4,039,269 A 8/1977 Pickering
4,048,474 A 9/1977 Olesen
4,049,954 A 9/1977 Da Costa Vieira et al.
4,055,175 A 10/1977 Clemens et al.
4,057,228 A 11/1977 Völker et al.
4,068,521 A 1/1978 Cosentino et al.
4,078,562 A 3/1978 Friedman
4,089,227 A 5/1978 Falgari et al.
4,094,318 A 6/1978 Burke
4,105,028 A 8/1978 Sadlier et al.
4,114,144 A 9/1978 Hyman
4,151,845 A 5/1979 Clemens
4,155,362 A 5/1979 Jess
4,164,986 A 8/1979 Eloy
4,173,224 A 11/1979 Marx
4,181,610 A 1/1980 Shintani et al.
4,183,244 A 1/1980 Kohno et al.
4,195,515 A 4/1980 Smoll
4,210,138 A 7/1980 Jess et al.
4,213,454 A 7/1980 Shim
4,217,993 A 8/1980 Jess et al.
4,240,294 A 12/1980 Grande
4,240,438 A 12/1980 Updike et al.
4,244,365 A 1/1981 McGill
4,256,437 A 3/1981 Brown
4,261,356 A 4/1981 Turner et al.
4,264,861 A 4/1981 Radu et al.
4,265,240 A 5/1981 Jenkins
4,270,532 A 6/1981 Franetzki et al.
4,277,226 A 7/1981 Archibald et al.
4,278,085 A 7/1981 Shim
4,280,495 A 7/1981 Lampert
4,282,872 A 8/1981 Franetzki et al.
4,286,202 A 8/1981 Clancy et al.
4,290,346 A 9/1981 Bujan
4,291,692 A 9/1981 Bowman et al.
4,292,405 A 9/1981 Mascoli
4,298,357 A 11/1981 Permic
4,308,866 A 1/1982 Jeliffe
4,312,341 A 1/1982 Zissimopoulos
4,319,568 A 3/1982 Tregoning
4,322,201 A 3/1982 Archibald
4,323,849 A 4/1982 Smith
4,324,662 A 4/1982 Schnell
4,328,800 A 5/1982 Marx
4,328,801 A 5/1982 Marx
4,333,045 A 6/1982 Oltendorf
4,343,316 A 8/1982 Jespersen
4,344,429 A 8/1982 Gupton et al.
4,346,707 A 8/1982 Whitney et al.
4,360,019 A 11/1982 Portner et al.
4,366,384 A 12/1982 Jensen
4,367,736 A 1/1983 Gupton
4,370,983 A 2/1983 Lichtenstein et al.
4,373,527 A 2/1983 Fischell
4,379,452 A 4/1983 DeVries
4,381,005 A 4/1983 Bujan
4,384,578 A 5/1983 Winkler
4,385,247 A 5/1983 Satomi
4,391,598 A 7/1983 Thompson
4,392,849 A 7/1983 Petre et al.
4,394,862 A 7/1983 Shim
4,395,259 A 7/1983 Prestele et al.
4,397,194 A 8/1983 Soltz
4,399,362 A 8/1983 Cormier et al.
4,407,659 A 10/1983 Adam
4,411,651 A 10/1983 Schulman
4,418,565 A 12/1983 St. John
4,432,699 A 2/1984 Beckman et al.
4,432,761 A 2/1984 Dawe
4,432,762 A 2/1984 Dawe
4,443,218 A 4/1984 Decant, Jr. et al.
4,444,546 A 4/1984 Pazemenas
4,447,191 A 5/1984 Bilstad et al.
4,447,224 A 5/1984 Decant, Jr. et al.
4,453,931 A 6/1984 Pastrone
4,457,751 A 7/1984 Rodler
4,463,301 A 7/1984 Moriguchi et al.
4,464,170 A 8/1984 Clemens
4,467,654 A 8/1984 Murakami et al.
4,468,222 A 8/1984 Lundquist
4,468,601 A 8/1984 Chamran et al.
4,469,481 A 9/1984 Kobayashi
4,475,666 A 10/1984 Bilbrey et al.
4,475,901 A 10/1984 Kraegen et al.
4,477,756 A 10/1984 Moriguchi
4,479,760 A 10/1984 Bilstad et al.
4,480,218 A 10/1984 Hair
4,480,483 A 11/1984 McShane
4,483,202 A 11/1984 Ogua et al.
4,487,601 A 12/1984 Lindemann
4,492,909 A 1/1985 Hartwig
4,496,346 A 1/1985 Mosteller
4,498,843 A 2/1985 Schneider et al.
4,501,531 A 2/1985 Bilstad et al.
4,504,263 A 3/1985 Steuer
4,507,112 A 3/1985 Hillel
4,510,266 A 4/1985 Eertink
4,513,796 A 4/1985 Miller et al.
4,515,584 A 5/1985 Abe et al.
4,519,792 A 5/1985 Dawe
4,521,212 A 6/1985 Ruschke
4,525,163 A 6/1985 Slavik et al.
4,526,568 A 7/1985 Clemens et al.
4,526,574 A 7/1985 Pekkarinen
4,529,401 A 7/1985 Leslie et al.
4,533,350 A 8/1985 Danby et al.
4,543,955 A 10/1985 Schroeppel
4,551,134 A 11/1985 Slavik et al.
4,553,958 A 11/1985 LeCocq
4,559,036 A 12/1985 Wunsch
4,559,037 A 12/1985 Franetzki et al.
4,559,044 A 12/1985 Robinson
4,559,454 A 12/1985 Kramer
4,565,500 A 1/1986 Jeensalute et al.

(56) References Cited

U.S. PATENT DOCUMENTS

| | | | |
|---|---|---|---|
| 4,583,981 | A | 4/1986 | Urquhart et al. |
| 4,587,473 | A | 5/1986 | Turvey |
| 4,607,520 | A | 8/1986 | Dam |
| 4,617,014 | A | 10/1986 | Cannon et al. |
| 4,624,661 | A | 11/1986 | Arimond |
| 4,627,835 | A | 12/1986 | Fenton, Jr. |
| 4,633,878 | A | 1/1987 | Bombardieri |
| 4,634,426 | A | 1/1987 | Kamen |
| 4,634,427 | A | 1/1987 | Hannula et al. |
| 4,636,144 | A | 1/1987 | Abe et al. |
| 4,637,813 | A | 1/1987 | DeVries |
| 4,645,489 | A | 2/1987 | Krumme |
| 4,648,869 | A | 3/1987 | Bobo, Jr. |
| 4,652,260 | A | 3/1987 | Fenton, Jr. et al. |
| 4,658,244 | A | 4/1987 | Meijer |
| 4,668,216 | A | 5/1987 | Martin |
| 4,668,945 | A | 5/1987 | Aldrovandi et al. |
| 4,673,334 | A | 6/1987 | Allington et al. |
| 4,673,389 | A | 6/1987 | Archibald et al. |
| 4,676,776 | A | 6/1987 | Howson et al. |
| 4,677,359 | A | 6/1987 | Enami et al. |
| 4,678,979 | A | 7/1987 | Hori |
| 4,678,998 | A | 7/1987 | Muramatsu |
| 4,679,562 | A | 7/1987 | Luksha |
| 4,683,428 | A | 7/1987 | Gete |
| 4,685,903 | A | 8/1987 | Cable et al. |
| 4,690,673 | A | 9/1987 | Blomquist |
| 4,691,153 | A | 9/1987 | Nishimura |
| 4,692,145 | A | 9/1987 | Weyant |
| 4,696,671 | A | 9/1987 | Epstein et al. |
| 4,697,129 | A | 9/1987 | Enami et al. |
| 4,702,675 | A | 10/1987 | Aldrovandi et al. |
| 4,705,506 | A | 11/1987 | Archibald et al. |
| 4,710,106 | A | 12/1987 | Iwata et al. |
| 4,714,462 | A | 12/1987 | DiDomenico |
| 4,714,463 | A | 12/1987 | Archibald et al. |
| 4,718,576 | A | 1/1988 | Tamura et al. |
| 4,720,636 | A | 1/1988 | Benner |
| 4,722,224 | A | 2/1988 | Scheller et al. |
| 4,722,734 | A | 2/1988 | Kolin |
| 4,731,051 | A | 3/1988 | Fischell |
| 4,731,057 | A | 3/1988 | Tanaka et al. |
| 4,737,711 | A | 4/1988 | O'Hare |
| 4,739,346 | A | 4/1988 | Buckley |
| 4,741,732 | A | 5/1988 | Crankshaw et al. |
| 4,741,736 | A | 5/1988 | Brown |
| 4,748,857 | A | 6/1988 | Nakagawa |
| 4,751,445 | A | 6/1988 | Sakai |
| 4,756,706 | A | 7/1988 | Kerns et al. |
| 4,758,228 | A | 7/1988 | Williams |
| 4,763,525 | A | 8/1988 | Cobb |
| 4,764,166 | A | 8/1988 | Spani et al. |
| 4,764,697 | A | 8/1988 | Christiaens |
| 4,769,001 | A | 9/1988 | Prince |
| 4,776,842 | A | 10/1988 | Franetzki et al. |
| 4,781,687 | A | 11/1988 | Wall |
| 4,784,576 | A | 11/1988 | Bloom et al. |
| 4,785,184 | A | 11/1988 | Bien et al. |
| 4,785,799 | A | 11/1988 | Schoon et al. |
| 4,785,969 | A | 11/1988 | McLaughlin |
| 4,786,800 | A | 11/1988 | Kamen |
| 4,789,014 | A | 12/1988 | DiGianfilippo |
| 4,797,655 | A | 1/1989 | Orndal et al. |
| 4,803,389 | A | 2/1989 | Ogawa et al. |
| 4,803,625 | A | 2/1989 | Fu et al. |
| 4,818,186 | A | 4/1989 | Pastrone et al. |
| 4,820,281 | A | 4/1989 | Lawler |
| 4,821,558 | A | 4/1989 | Pastrone et al. |
| 4,828,545 | A | 5/1989 | Epstein et al. |
| 4,828,693 | A | 5/1989 | Lindsay |
| 4,829,448 | A | 5/1989 | Balding et al. |
| 4,838,856 | A | 6/1989 | Mulreany et al. |
| 4,838,857 | A | 6/1989 | Strowe et al. |
| 4,840,542 | A | 6/1989 | Abbott |
| 4,842,584 | A | 6/1989 | Pastrone et al. |
| 4,845,487 | A | 7/1989 | Frantz et al. |
| 4,846,792 | A | 7/1989 | Bobo et al. |
| 4,850,805 | A | 7/1989 | Madsen et al. |
| 4,851,755 | A | 7/1989 | Fincher |
| 4,854,324 | A | 8/1989 | Hirschman et al. |
| 4,856,339 | A | 8/1989 | Williams |
| 4,857,048 | A | 8/1989 | Simons et al. |
| 4,857,050 | A | 8/1989 | Lentz et al. |
| 4,858,154 | A | 8/1989 | Anderson et al. |
| 4,863,425 | A | 9/1989 | Slate et al. |
| 4,865,584 | A | 9/1989 | Epstein et al. |
| 4,869,722 | A | 9/1989 | Heyman |
| 4,874,359 | A | 10/1989 | White et al. |
| 4,881,413 | A | 11/1989 | Georgi et al. |
| 4,882,575 | A | 11/1989 | Kawahara |
| 4,884,013 | A | 11/1989 | Jackson et al. |
| 4,884,065 | A | 11/1989 | Crouse et al. |
| 4,886,422 | A | 12/1989 | Takeuchi et al. |
| 4,898,576 | A | 2/1990 | Philip |
| 4,898,578 | A | 2/1990 | Rubalcaba, Jr. |
| 4,906,103 | A | 3/1990 | Kao |
| 4,908,017 | A | 3/1990 | Howson et al. |
| 4,908,019 | A | 3/1990 | Urquhart et al. |
| 4,910,475 | A | 3/1990 | Lin |
| 4,919,595 | A | 4/1990 | Likuski et al. |
| 4,919,596 | A | 4/1990 | Slate et al. |
| 4,925,444 | A | 5/1990 | Orkin et al. |
| 4,927,411 | A | 5/1990 | Pastrone et al. |
| 4,930,358 | A | 6/1990 | Motegi et al. |
| 4,936,820 | A | 6/1990 | Dennehey |
| 4,936,828 | A | 6/1990 | Chiang |
| 4,938,079 | A | 7/1990 | Goldberg |
| 4,943,279 | A | 7/1990 | Samiotes et al. |
| 4,946,439 | A | 8/1990 | Eggers |
| 4,947,856 | A | 8/1990 | Beard |
| 4,950,235 | A | 8/1990 | Slate et al. |
| 4,950,244 | A | 8/1990 | Fellingham |
| 4,959,050 | A | 9/1990 | Bobo, Jr. |
| 4,966,579 | A | 10/1990 | Polaschegg |
| 4,968,941 | A | 11/1990 | Rogers |
| 4,972,842 | A | 11/1990 | Korten et al. |
| 4,976,687 | A | 12/1990 | Martin |
| 4,978,335 | A | 12/1990 | Arthur, III |
| 4,979,940 | A | 12/1990 | Lapp et al. |
| 4,981,467 | A | 1/1991 | Bobo et al. |
| 5,000,663 | A | 3/1991 | Gorton |
| 5,000,739 | A | 3/1991 | Kulisz et al. |
| 5,006,050 | A | 4/1991 | Cooke et al. |
| 5,010,473 | A | 4/1991 | Jacobs |
| 5,014,714 | A | 5/1991 | Millay et al. |
| 5,014,798 | A | 5/1991 | Glynn |
| 5,018,945 | A | 5/1991 | D'Silva |
| 5,026,348 | A | 6/1991 | Venegas |
| 5,028,857 | A | 7/1991 | Taghezout |
| 5,032,112 | A | 7/1991 | Fairchild et al. |
| 5,034,004 | A | 7/1991 | Crankshaw |
| 5,035,143 | A | 7/1991 | Latimer et al. |
| 5,040,699 | A | 8/1991 | Gangemi |
| 5,041,086 | A | 8/1991 | Koenig et al. |
| 5,043,706 | A | 8/1991 | Oliver |
| 5,045,069 | A | 9/1991 | Imparato |
| 5,049,047 | A | 9/1991 | Polaschegg et al. |
| 5,052,230 | A | 10/1991 | Lang |
| 5,053,747 | A | 10/1991 | Slate et al. |
| 5,055,761 | A | 10/1991 | Mills |
| 5,056,992 | A | 10/1991 | Simons |
| 5,058,161 | A | 10/1991 | Weiss |
| 5,059,171 | A | 10/1991 | Bridge |
| 5,063,603 | A | 11/1991 | Burt |
| 5,064,412 | A | 11/1991 | Henke et al. |
| 5,078,683 | A | 1/1992 | Sancoff et al. |
| 5,084,663 | A | 1/1992 | Olsson |
| 5,084,828 | A | 1/1992 | Kaufman et al. |
| 5,088,981 | A | 2/1992 | Howson et al. |
| 5,096,385 | A | 3/1992 | Georgi et al. |
| 5,097,505 | A | 3/1992 | Weiss |
| 5,100,380 | A | 3/1992 | Epstein et al. |
| 5,102,392 | A | 4/1992 | Sakai et al. |
| 5,103,211 | A | 4/1992 | Daoud et al. |

(56) References Cited

U.S. PATENT DOCUMENTS

| | | | |
|---|---|---|---|
| 5,104,374 | A | 4/1992 | Bishko et al. |
| 5,108,367 | A | 4/1992 | Epstein et al. |
| 5,109,850 | A | 5/1992 | Blanco et al. |
| 5,116,203 | A | 5/1992 | Nartwick et al. |
| 5,116,312 | A | 5/1992 | Blakenship et al. |
| 5,116,316 | A | 5/1992 | Sertic |
| 5,123,275 | A | 6/1992 | Daoud et al. |
| 5,124,627 | A | 6/1992 | Okada |
| 5,125,499 | A | 6/1992 | Saathoff et al. |
| 5,131,816 | A | 7/1992 | Brown |
| 5,132,603 | A | 7/1992 | Yoshimoto |
| 5,153,827 | A | 10/1992 | Coutre et al. |
| 5,158,441 | A | 10/1992 | Aid |
| 5,161,222 | A | 11/1992 | Montejo et al. |
| 5,174,472 | A | 12/1992 | Raque et al. |
| 5,176,631 | A | 1/1993 | Koenig |
| 5,176,646 | A | 1/1993 | Kuroda |
| 5,179,340 | A | 1/1993 | Rogers |
| 5,180,287 | A | 1/1993 | Natwick et al. |
| 5,181,910 | A | 1/1993 | Scanlon |
| 5,186,057 | A | 2/1993 | Everhart |
| 5,188,603 | A | 2/1993 | Vaillancourt |
| 5,190,522 | A | 3/1993 | Wocicki et al. |
| 5,191,795 | A | 3/1993 | Fellingham et al. |
| 5,192,340 | A | 3/1993 | Grant et al. |
| 5,194,796 | A | 3/1993 | Domeki et al. |
| 5,198,776 | A | 3/1993 | Carr |
| 5,200,090 | A | 4/1993 | Ford |
| 5,205,819 | A | 4/1993 | Ross et al. |
| 5,206,522 | A | 4/1993 | Danby et al. |
| 5,207,642 | A | 5/1993 | Orkin et al. |
| 5,211,626 | A | 5/1993 | Frank et al. |
| 5,213,573 | A | 5/1993 | Sorich et al. |
| 5,215,450 | A | 6/1993 | Tamari |
| 5,216,597 | A | 6/1993 | Beckers |
| 5,219,099 | A | 6/1993 | Spence et al. |
| 5,219,327 | A | 6/1993 | Okada |
| 5,221,268 | A | 6/1993 | Barton et al. |
| 5,229,713 | A | 7/1993 | Bullock et al. |
| 5,232,476 | A | 8/1993 | Grant |
| 5,233,571 | A | 8/1993 | Wirtschafter |
| 5,237,309 | A | 8/1993 | Frantz et al. |
| 5,242,406 | A | 9/1993 | Gross et al. |
| 5,242,408 | A | 9/1993 | Jhuboo et al. |
| 5,243,982 | A | 9/1993 | Möstl et al. |
| 5,244,463 | A | 9/1993 | Cordner, Jr. et al. |
| 5,244,568 | A | 9/1993 | Lindsay et al. |
| 5,254,096 | A | 10/1993 | Rondelet et al. |
| 5,256,155 | A | 10/1993 | Yerlikaya et al. |
| 5,256,156 | A | 10/1993 | Kern et al. |
| 5,256,157 | A | 10/1993 | Samiotes et al. |
| 5,257,206 | A | 10/1993 | Hanson |
| 5,260,665 | A | 11/1993 | Goldberg |
| 5,262,944 | A | 11/1993 | Weisner et al. |
| 5,267,980 | A | 12/1993 | Dirr et al. |
| 5,274,316 | A | 12/1993 | Evans et al. |
| 5,276,610 | A | 1/1994 | Maeda et al. |
| 5,280,728 | A | 1/1994 | Sato et al. |
| 5,283,510 | A | 2/1994 | Tamaki et al. |
| 5,287,851 | A | 2/1994 | Beran et al. |
| 5,292,306 | A | 3/1994 | Wynkoop et al. |
| 5,295,967 | A | 3/1994 | Rondelet et al. |
| 5,298,021 | A | 3/1994 | Sherer |
| 5,303,585 | A | 4/1994 | Lichte |
| 5,304,126 | A | 4/1994 | Epstein et al. |
| 5,304,216 | A | 4/1994 | Wallace |
| 5,308,333 | A | 5/1994 | Skakoon |
| 5,317,506 | A | 5/1994 | Coutre et al. |
| 5,319,363 | A | 6/1994 | Welch et al. |
| 5,319,979 | A | 6/1994 | Abrahamson |
| 5,321,392 | A | 6/1994 | Skakoon et al. |
| 5,325,170 | A | 6/1994 | Bornhop |
| 5,325,728 | A | 7/1994 | Zimmerman et al. |
| 5,328,460 | A | 7/1994 | Lord et al. |
| 5,330,634 | A | 7/1994 | Wong et al. |
| 5,333,497 | A | 8/1994 | Braend et al. |
| 5,336,051 | A | 8/1994 | Tamari |
| 5,338,157 | A | 8/1994 | Blomquist |
| 5,342,298 | A | 8/1994 | Michaels |
| 5,343,734 | A | 9/1994 | Maeda et al. |
| 5,343,885 | A | 9/1994 | Grant |
| 5,346,466 | A | 9/1994 | Yerlikaya et al. |
| 5,356,378 | A | 10/1994 | Doan et al. |
| 5,359,271 | A | 10/1994 | Husher |
| D352,778 | S | 11/1994 | Irvin et al. |
| 5,364,346 | A | 11/1994 | Schrezenmeir |
| 5,366,346 | A | 11/1994 | Danby |
| 5,368,562 | A | 11/1994 | Blomquist et al. |
| 5,374,865 | A | 12/1994 | Yoshimura et al. |
| 5,376,070 | A | 12/1994 | Purvis et al. |
| 5,378,231 | A | 1/1995 | Johnson et al. |
| 5,382,232 | A | 1/1995 | Hague et al. |
| 5,383,369 | A | 1/1995 | Khuri-Yakub et al. |
| 5,389,071 | A | 2/1995 | Kawahara et al. |
| 5,389,078 | A | 2/1995 | Zalesky et al. |
| 5,392,638 | A | 2/1995 | Kawahara |
| 5,394,732 | A | 3/1995 | Johnson et al. |
| 5,395,320 | A | 3/1995 | Padda et al. |
| 5,399,171 | A | 3/1995 | Bowman et al. |
| 5,406,954 | A | 4/1995 | Tomita |
| 5,408,326 | A | 4/1995 | Priestley |
| 5,415,528 | A | 5/1995 | Ogden et al. |
| 5,417,119 | A | 5/1995 | Smoll |
| 5,417,222 | A | 5/1995 | Dempsey et al. |
| 5,417,395 | A | 5/1995 | Fowler et al. |
| 5,418,443 | A | 5/1995 | Kikuchi |
| 5,421,208 | A | 6/1995 | Packard et al. |
| 5,423,748 | A | 6/1995 | Uhala |
| 5,423,749 | A | 6/1995 | Merte et al. |
| 5,423,759 | A | 6/1995 | Campbell |
| 5,428,284 | A | 6/1995 | Kaneda et al. |
| 5,429,485 | A | 7/1995 | Dodge |
| 5,429,601 | A | 7/1995 | Conley |
| 5,429,602 | A | 7/1995 | Hauser |
| 5,431,627 | A | 7/1995 | Pastrone et al. |
| 5,434,508 | A | 7/1995 | Ishida |
| 5,437,624 | A | 8/1995 | Langley et al. |
| 5,444,316 | A | 8/1995 | Ohya et al. |
| 5,444,378 | A | 8/1995 | Rogers |
| 5,445,621 | A | 8/1995 | Poli et al. |
| 5,450,758 | A | 9/1995 | Smoll |
| 5,451,881 | A | 9/1995 | Finger |
| 5,455,423 | A | 10/1995 | Mount et al. |
| 5,455,851 | A | 10/1995 | Chaco et al. |
| 5,463,906 | A | 11/1995 | Spani et al. |
| 5,464,392 | A | 11/1995 | Epstein et al. |
| 5,465,082 | A | 11/1995 | Chaco |
| 5,469,851 | A | 11/1995 | Lipschutz |
| 5,473,948 | A | 12/1995 | Moss et al. |
| 5,480,294 | A | 1/1996 | Di Perna et al. |
| 5,482,438 | A | 1/1996 | Anderson et al. |
| 5,485,408 | A | 1/1996 | Blomquist |
| 5,486,286 | A | 1/1996 | Peterson et al. |
| 5,489,265 | A | 2/1996 | Montalvo et al. |
| 5,495,566 | A | 2/1996 | Kwatinetz |
| 5,496,273 | A | 3/1996 | Pastrone et al. |
| 5,505,696 | A | 4/1996 | Miki |
| 5,505,828 | A | 4/1996 | Wong et al. |
| 5,507,288 | A | 4/1996 | Bocker et al. |
| 5,507,412 | A | 4/1996 | Ebert et al. |
| 5,520,637 | A | 5/1996 | Pager et al. |
| 5,522,798 | A | 6/1996 | Johnson et al. |
| 5,522,799 | A | 6/1996 | Furukawa |
| 5,527,344 | A | 6/1996 | Arzbaecher et al. |
| 5,527,630 | A | 6/1996 | Nagata |
| 5,533,389 | A | 7/1996 | Kamen et al. |
| 5,537,853 | A | 7/1996 | Finburgh et al. |
| 5,542,040 | A | 7/1996 | Chang et al. |
| 5,545,140 | A | 8/1996 | Conero et al. |
| 5,547,470 | A | 8/1996 | Johnson et al. |
| 5,551,850 | A | 9/1996 | Williamson et al. |
| 5,554,013 | A | 9/1996 | Owens et al. |
| 5,554,115 | A | 9/1996 | Thomas et al. |
| 5,558,638 | A | 9/1996 | Evers et al. |

(56) References Cited

U.S. PATENT DOCUMENTS 5,562,615 A 10/1996 Nassif
5,563,486 A 10/1996 Yamamoto et al.
5,572,105 A 11/1996 Nojima et al.
5,573,502 A 11/1996 LeCocq et al.
5,583,280 A 12/1996 Mo et al.
5,584,667 A 12/1996 Davis
5,584,806 A 12/1996 Amano
5,586,868 A 12/1996 Lawless et al.
5,590,653 A 1/1997 Aida et al.
5,594,786 A 1/1997 Chaco et al.
5,600,073 A 2/1997 Hill
5,601,420 A 2/1997 Warner et al.
5,609,575 A 3/1997 Larson et al.
5,609,576 A 3/1997 Voss
5,611,784 A 3/1997 Barresi et al.
5,616,124 A 4/1997 Hague et al.
5,620,312 A 4/1997 Hyman et al.
5,620,608 A 4/1997 Rosa et al.
5,626,140 A 5/1997 Feldman et al.
5,626,151 A 5/1997 Linden
5,626,563 A 5/1997 Dodge et al.
5,627,443 A 5/1997 Kimura et al.
5,628,309 A 5/1997 Brown
5,628,731 A 5/1997 Dodge et al.
5,630,710 A 5/1997 Tune et al.
5,634,896 A 6/1997 Bryant et al.
5,637,095 A 6/1997 Nason et al.
5,640,075 A 6/1997 Brasseur et al.
5,640,150 A 6/1997 Atwater
5,643,212 A 7/1997 Coutre et al.
5,648,710 A 7/1997 Ikeda
5,649,536 A 7/1997 Ogura et al.
5,651,775 A 7/1997 Walker et al.
5,657,000 A 8/1997 Ellingboe
5,658,133 A 8/1997 Anderson et al.
5,658,250 A 8/1997 Blomquist et al.
5,659,234 A 8/1997 Cresens
5,661,245 A 8/1997 Svoboda et al.
D384,052 S 9/1997 Kodosky
5,662,612 A 9/1997 Niehoff
5,665,065 A 9/1997 Colman et al.
5,669,877 A 9/1997 Blomquist
5,672,154 A 9/1997 Sillén et al.
5,672,832 A 9/1997 Cucci et al.
5,681,285 A 10/1997 Ford et al.
5,681,286 A 10/1997 Niehoff
5,685,844 A 11/1997 Marttila
5,685,866 A 11/1997 Lopez
5,687,717 A 11/1997 Halpern et al.
5,689,229 A 11/1997 Chaco et al.
5,691,613 A 11/1997 Gutwillinger
5,695,464 A 12/1997 Viallet
5,695,473 A 12/1997 Olsen
5,697,899 A 12/1997 Hillman et al.
5,697,916 A 12/1997 Schraga
5,712,795 A 1/1998 Layman et al.
5,713,856 A 2/1998 Eggers et al.
5,714,691 A 2/1998 Hill
5,718,562 A 2/1998 Lawless et al.
5,718,569 A 2/1998 Holst
5,720,721 A 2/1998 Dumas et al.
5,722,417 A 3/1998 Rudolph
5,728,074 A 3/1998 Castellano et al.
5,728,948 A 3/1998 Bignell et al.
5,733,257 A 3/1998 Stemby
5,733,259 A 3/1998 Valcke et al.
5,734,464 A 3/1998 Gibbs
5,738,659 A 4/1998 Neer et al.
5,743,856 A 4/1998 Oka et al.
5,744,027 A 4/1998 Connell et al.
5,744,929 A 4/1998 Miyazaki
5,745,378 A 4/1998 Barker et al.
5,752,813 A 5/1998 Tyner et al.
5,752,918 A 5/1998 Fowler et al.
5,752,919 A 5/1998 Schrimpf
5,755,691 A 5/1998 Hilborne
5,758,643 A 6/1998 Wong et al.
5,761,072 A 6/1998 Bardsley, Jr. et al.
5,764,034 A 6/1998 Bowman et al.
5,766,155 A 6/1998 Hyman et al.
5,772,635 A 6/1998 Dastur et al.
5,778,256 A 7/1998 Darbee
5,781,442 A 7/1998 Engleson et al.
5,782,805 A 7/1998 Meinzer et al.
5,788,669 A 8/1998 Peterson
5,788,674 A 8/1998 McWilliams
5,789,923 A 8/1998 Shimoyama et al.
5,792,069 A 8/1998 Greenwald et al.
5,793,211 A 8/1998 Shimoyama et al.
5,795,327 A 8/1998 Wilson et al.
5,798,934 A 8/1998 Saigo et al.
5,800,387 A 9/1998 Duffy et al.
5,803,712 A 9/1998 Davis et al.
5,803,917 A 9/1998 Butterfield
5,805,455 A 9/1998 Lipps
5,807,322 A 9/1998 Lindsey et al.
5,810,770 A 9/1998 Chin et al.
5,813,972 A 9/1998 Nazarian et al.
5,814,004 A 9/1998 Tamari
5,814,015 A 9/1998 Gargano et al.
5,816,779 A 10/1998 Lawless et al.
5,822,715 A 10/1998 Worthington et al.
5,827,179 A 10/1998 Lichter et al.
5,827,223 A 10/1998 Butterfield
5,832,448 A 11/1998 Brown
5,836,910 A 11/1998 Duffy et al.
5,841,261 A 11/1998 Nojima et al.
5,841,284 A 11/1998 Takahashi
5,843,035 A 12/1998 Bowman
5,848,971 A 12/1998 Fowler et al.
5,850,344 A 12/1998 Conkright
5,857,843 A 1/1999 Leason et al.
5,864,330 A 1/1999 Haynes
5,865,805 A 2/1999 Ziemba
5,867,821 A 2/1999 Ballantyne et al.
5,871,465 A 2/1999 Vasko
5,872,453 A 2/1999 Shimoyama et al.
5,875,195 A 2/1999 Dixon
5,882,300 A 3/1999 Malinouskas et al.
5,882,339 A 3/1999 Beiser et al.
5,885,245 A 3/1999 Lynch et al.
5,889,379 A 3/1999 Yanagi et al.
5,891,051 A 4/1999 Han et al.
5,894,209 A 4/1999 Takagi et al.
5,897,493 A 4/1999 Brown
5,897,498 A 4/1999 Canfield, II et al.
5,898,292 A 4/1999 Takemoto et al.
5,899,665 A 5/1999 Makino et al.
5,901,150 A 5/1999 Jhuboo et al.
5,904,666 A 5/1999 DeDecker et al.
5,904,668 A 5/1999 Hyman et al.
5,905,207 A 5/1999 Schalk
5,906,598 A 5/1999 Giesier
5,910,252 A 6/1999 Truitt et al.
5,915,240 A 6/1999 Karpf
5,920,263 A 7/1999 Huttenhoff et al.
5,923,159 A 7/1999 Ezell
5,924,074 A 7/1999 Evans
5,927,349 A 7/1999 Martucci
5,932,119 A 8/1999 Kaplan et al.
5,932,987 A 8/1999 McLoughlin
5,935,066 A 8/1999 Harris
5,935,099 A 8/1999 Peterson et al.
5,935,106 A 8/1999 Olsen
5,938,634 A 8/1999 Packard
5,938,636 A 8/1999 Kramer et al.
5,941,846 A 8/1999 Duffy et al.
5,944,660 A 8/1999 Kimball et al.
5,947,911 A 9/1999 Wong et al.
5,954,527 A 9/1999 Jhuboo et al.
5,954,696 A 9/1999 Ryan et al.
5,956,023 A 9/1999 Lyle et al.
5,956,501 A 9/1999 Brown
5,957,885 A 9/1999 Bollish et al.

(56) References Cited

U.S. PATENT DOCUMENTS

| | | | |
|---|---|---|---|
| 5,957,890 | A | 9/1999 | Mann et al. |
| 5,971,594 | A | 10/1999 | Sahai et al. |
| 5,973,497 | A | 10/1999 | Bergk et al. |
| 5,975,081 | A | 11/1999 | Hood et al. |
| 5,989,222 | A | 11/1999 | Cole et al. |
| 5,990,838 | A | 11/1999 | Burns et al. |
| 5,991,525 | A | 11/1999 | Shah et al. |
| 5,993,393 | A | 11/1999 | Ryan et al. |
| 5,994,876 | A | 11/1999 | Canny et al. |
| 5,997,476 | A | 12/1999 | Brown |
| 6,000,828 | A | 12/1999 | Leet |
| 6,003,006 | A | 12/1999 | Colella et al. |
| 6,003,388 | A | 12/1999 | Oeftering |
| 6,012,034 | A | 1/2000 | Hamparian et al. |
| 6,017,318 | A | 1/2000 | Gauthier et al. |
| 6,017,493 | A | 1/2000 | Cambron |
| 6,021,392 | A | 2/2000 | Lester et al. |
| 6,023,977 | A | 2/2000 | Langdon et al. |
| 6,024,539 | A | 2/2000 | Blomquist |
| 6,027,441 | A | 2/2000 | Cantu |
| 6,028,412 | A | 2/2000 | Shine et al. |
| 6,032,676 | A | 3/2000 | Moore |
| 6,033,561 | A | 3/2000 | Schoendorfer |
| 6,036,017 | A | 3/2000 | Bayliss, IV |
| 6,068,612 | A | 5/2000 | Bowman |
| 6,068,615 | A | 5/2000 | Brown et al. |
| 6,073,106 | A | 6/2000 | Rozen et al. |
| 6,077,246 | A | 6/2000 | Kullas et al. |
| 6,083,206 | A | 7/2000 | Molko |
| 6,089,104 | A | 7/2000 | Chang |
| 6,104,295 | A | 8/2000 | Gaisser et al. |
| 6,110,152 | A | 8/2000 | Kovelman |
| 6,110,153 | A | 8/2000 | Davis |
| RE36,871 | E | 9/2000 | Epstein et al. |
| 6,120,459 | A | 9/2000 | Nitzan et al. |
| 6,122,536 | A | 9/2000 | Sun et al. |
| 6,142,008 | A | 11/2000 | Cole et al. |
| 6,150,942 | A | 11/2000 | O'Brien |
| 6,157,914 | A | 12/2000 | Seto et al. |
| 6,158,288 | A | 12/2000 | Smith |
| 6,158,965 | A | 12/2000 | Butterfield et al. |
| 6,159,147 | A | 12/2000 | Lichter et al. |
| 6,159,186 | A | 12/2000 | Wickham et al. |
| 6,164,921 | A | 12/2000 | Moubayed et al. |
| 6,168,561 | B1 | 1/2001 | Cantu |
| 6,178,827 | B1 | 1/2001 | Feller |
| 6,182,667 | B1 | 2/2001 | Hanks et al. |
| 6,186,141 | B1 | 2/2001 | Pike et al. |
| 6,189,105 | B1 | 2/2001 | Lopes |
| 6,192,752 | B1 | 2/2001 | Blaine |
| 6,195,589 | B1 | 2/2001 | Ketcham |
| 6,202,711 | B1 | 3/2001 | Martucci |
| 6,203,528 | B1 | 3/2001 | Deckert |
| 6,208,107 | B1 | 3/2001 | Maske et al. |
| 6,212,936 | B1 | 4/2001 | Meisberger |
| 6,213,972 | B1 | 4/2001 | Butterfield |
| 6,231,320 | B1 | 5/2001 | Lawless et al. |
| 6,234,176 | B1 | 5/2001 | Domae et al. |
| 6,236,326 | B1 | 5/2001 | Murphy et al. |
| 6,237,398 | B1 | 5/2001 | Porat et al. |
| 6,241,704 | B1 | 6/2001 | Peterson et al. |
| 6,248,067 | B1 | 6/2001 | Causey, III et al. |
| 6,250,132 | B1 | 6/2001 | Drzewiecki |
| 6,259,355 | B1 | 7/2001 | Chaco et al. |
| 6,259,587 | B1 | 7/2001 | Sheldon et al. |
| 6,261,065 | B1 | 7/2001 | Nayak |
| 6,262,946 | B1 | 7/2001 | Khuri-Yakub et al. |
| 6,267,559 | B1 | 7/2001 | Mossman et al. |
| 6,267,725 | B1 | 7/2001 | Dubberstein et al. |
| 6,269,340 | B1 | 7/2001 | Ford et al. |
| 6,270,455 | B1 | 8/2001 | Brown |
| 6,271,813 | B1 | 8/2001 | Palalau |
| 6,277,072 | B1 | 8/2001 | Bardy |
| 6,277,099 | B1 | 8/2001 | Strowe et al. |
| 6,280,380 | B1 | 8/2001 | Bardy |
| 6,280,391 | B1 | 8/2001 | Olson et al. |
| 6,280,408 | B1 | 8/2001 | Sipin |
| 6,283,761 | B1 | 9/2001 | Joao |
| 6,285,155 | B1 | 9/2001 | Maske et al. |
| 6,312,378 | B1 | 11/2001 | Bardy |
| 6,322,516 | B1 | 11/2001 | Masuda et al. |
| 6,330,351 | B1 | 12/2001 | Yasunaga |
| 6,336,053 | B1 | 1/2002 | Beatty |
| 6,337,675 | B1 | 1/2002 | Toffolo et al. |
| 6,345,539 | B1 | 2/2002 | Rawes et al. |
| 6,347,553 | B1 | 2/2002 | Morris et al. |
| 6,349,740 | B1 | 2/2002 | Cho et al. |
| 6,358,225 | B1 | 3/2002 | Butterfield |
| 6,358,387 | B1 | 3/2002 | Kopf-Sill et al. |
| 6,362,591 | B1 | 3/2002 | Moberg |
| 6,385,505 | B1 | 5/2002 | Lipps |
| 6,386,050 | B1 | 5/2002 | Yin et al. |
| 6,394,958 | B1 | 5/2002 | Bratteli et al. |
| 6,396,583 | B1 | 5/2002 | Clare |
| D459,362 | S | 6/2002 | Platz |
| 6,398,760 | B1 | 6/2002 | Danby |
| 6,405,076 | B1 | 6/2002 | Taylor et al. |
| 6,408,679 | B1 | 6/2002 | Kline-Schoder et al. |
| 6,409,699 | B1 | 6/2002 | Ash |
| 6,413,238 | B1 | 7/2002 | Maget |
| 6,416,291 | B1 | 7/2002 | Butterfield et al. |
| 6,418,334 | B1 | 7/2002 | Unger et al. |
| 6,418,535 | B1 | 7/2002 | Kulakowski et al. |
| 6,445,053 | B1 | 9/2002 | Cho |
| 6,456,245 | B1 | 9/2002 | Crawford |
| 6,457,346 | B1 | 10/2002 | Kline-Schoder et al. |
| 6,463,785 | B1 | 10/2002 | Kline-Schoder et al. |
| 6,467,331 | B1 | 10/2002 | Kline-Schoder et al. |
| 6,468,242 | B1 | 10/2002 | Wilson et al. |
| 6,475,178 | B1 | 11/2002 | Krajewski |
| 6,481,980 | B1 | 11/2002 | Vandlik |
| 6,482,158 | B2 | 11/2002 | Mault |
| 6,482,185 | B1 | 11/2002 | Hartmann |
| 6,485,263 | B1 | 11/2002 | Bryant et al. |
| 6,485,418 | B2 | 11/2002 | Yasushi et al. |
| 6,485,465 | B2 | 11/2002 | Moberg et al. |
| 6,487,916 | B1 | 12/2002 | Gomm et al. |
| 6,489,896 | B1 | 12/2002 | Platt |
| 6,494,694 | B2 | 12/2002 | Lawless et al. |
| 6,494,831 | B1 | 12/2002 | Koritzinsky |
| 6,497,680 | B1 | 12/2002 | Holst et al. |
| 6,503,221 | B1 | 1/2003 | Briggs |
| 6,512,944 | B1 | 1/2003 | Kovtun et al. |
| 6,516,667 | B1 | 2/2003 | Broad et al. |
| 6,517,482 | B1 | 2/2003 | Eiden et al. |
| 6,519,569 | B1 | 2/2003 | White et al. |
| 6,529,751 | B1 | 3/2003 | Van Driel et al. |
| 6,531,708 | B1 | 3/2003 | Malmstrom |
| 6,539,315 | B1 | 3/2003 | Adams et al. |
| D473,238 | S | 4/2003 | Cockerill |
| 6,540,672 | B1 | 4/2003 | Simonsen et al. |
| 6,544,212 | B2 | 4/2003 | Galley et al. |
| 6,544,228 | B1 | 4/2003 | Heitmeier |
| 6,558,125 | B1 | 5/2003 | Futterknecht |
| 6,558,351 | B1 | 5/2003 | Steil et al. |
| 6,562,012 | B1 | 5/2003 | Brown et al. |
| 6,564,825 | B2 | 5/2003 | Lowery et al. |
| 6,565,509 | B1 | 5/2003 | Say et al. |
| 6,568,416 | B2 | 5/2003 | Tucker et al. |
| 6,572,542 | B1 | 6/2003 | Houben et al. |
| 6,572,545 | B2 | 6/2003 | Knobbe et al. |
| 6,572,576 | B2 | 6/2003 | Brugger et al. |
| 6,578,422 | B2 | 6/2003 | Lam et al. |
| 6,578,435 | B2 | 6/2003 | Gould et al. |
| 6,581,117 | B1 | 6/2003 | Klein et al. |
| RE38,189 | E | 7/2003 | Walker et al. |
| 6,585,675 | B1 | 7/2003 | O'Mahony et al. |
| 6,589,229 | B1 | 7/2003 | Connelly et al. |
| 6,589,792 | B1 | 7/2003 | Malachowski |
| 6,599,281 | B1 | 7/2003 | Struys et al. |
| 6,599,282 | B2 | 7/2003 | Burko |
| 6,602,191 | B2 | 8/2003 | Quy |
| 6,605,072 | B2 | 8/2003 | Struys et al. |
| 6,606,047 | B1 | 8/2003 | Börjesson et al. |

(56) References Cited

U.S. PATENT DOCUMENTS

| | | | |
|---|---|---|---|
| 6,609,047 | B1 | 8/2003 | Lipps |
| 6,615,674 | B2 | 9/2003 | Ohnishi |
| 6,616,633 | B1 | 9/2003 | Butterfield et al. |
| 6,617,564 | B2 | 9/2003 | Ockerse et al. |
| 6,618,916 | B1 | 9/2003 | Eberle et al. |
| 6,622,542 | B2 | 9/2003 | Derek |
| 6,622,561 | B2 | 9/2003 | Lam et al. |
| D481,121 | S | 10/2003 | Evans |
| 6,629,449 | B1 | 10/2003 | Kline-Schoder et al. |
| 6,634,233 | B2 | 10/2003 | He |
| 6,640,246 | B1 | 10/2003 | Gardy, Jr. et al. |
| 6,641,533 | B2 | 11/2003 | Causey, III et al. |
| 6,641,541 | B1 | 11/2003 | Lovett et al. |
| 6,648,861 | B2 | 11/2003 | Platt et al. |
| 6,652,455 | B1 | 11/2003 | Kocher |
| 6,653,937 | B2 | 11/2003 | Nelson et al. |
| 6,659,980 | B2 | 12/2003 | Moberg et al. |
| D485,356 | S | 1/2004 | Evans |
| 6,685,668 | B1 | 2/2004 | Cho et al. |
| 6,685,678 | B2 | 2/2004 | Evans et al. |
| 6,689,069 | B2 | 2/2004 | Bratteli et al. |
| 6,689,091 | B2 | 2/2004 | Bui et al. |
| 6,692,241 | B2 | 2/2004 | Watanabe et al. |
| D487,574 | S | 3/2004 | Glaser |
| 6,716,004 | B2 | 4/2004 | Vandlik |
| 6,719,535 | B2 | 4/2004 | Rakestraw et al. |
| 6,721,582 | B2 | 4/2004 | Trepagnier et al. |
| 6,722,211 | B1 | 4/2004 | Ciobanu et al. |
| 6,725,200 | B1 | 4/2004 | Rost |
| 6,725,721 | B2 | 4/2004 | Venczel |
| 6,731,989 | B2 | 5/2004 | Engleson et al. |
| 6,732,595 | B2 | 5/2004 | Lynnworth |
| 6,738,052 | B1 | 5/2004 | Manke et al. |
| 6,740,072 | B2 | 5/2004 | Starkweather et al. |
| 6,741,212 | B2 | 5/2004 | Kralovec et al. |
| 6,748,808 | B2 | 6/2004 | Lam et al. |
| 6,749,403 | B2 | 6/2004 | Bryant et al. |
| 6,752,787 | B1 | 6/2004 | Causey, III et al. |
| 6,753,842 | B1 | 6/2004 | Williams et al. |
| 6,759,007 | B1 | 7/2004 | Westberg |
| 6,760,643 | B2 | 7/2004 | Lipps |
| 6,768,920 | B2 | 7/2004 | Lange |
| 6,773,412 | B2 | 8/2004 | O'Mahony |
| 6,780,156 | B2 | 8/2004 | Haueter et al. |
| 6,783,328 | B2 | 8/2004 | Lucke et al. |
| 6,785,573 | B2 | 8/2004 | Kovtun et al. |
| 6,786,885 | B2 | 9/2004 | Hochman et al. |
| 6,789,426 | B2 | 9/2004 | Yaralioglu et al. |
| 6,790,198 | B1 | 9/2004 | White et al. |
| 6,793,625 | B2 | 9/2004 | Cavallaro et al. |
| 6,801,227 | B2 | 10/2004 | Bocionek et al. |
| 6,805,671 | B2 | 10/2004 | Stergiopoulos et al. |
| 6,807,965 | B1 | 10/2004 | Hickle |
| 6,809,653 | B1 | 10/2004 | Mann et al. |
| 6,813,964 | B1 | 11/2004 | Clark et al. |
| 6,814,547 | B2 | 11/2004 | Childers |
| 6,824,528 | B1 | 11/2004 | Faries |
| 6,830,558 | B2 | 12/2004 | Flaherty et al. |
| 6,840,113 | B2 | 1/2005 | Fukumura et al. |
| 6,846,161 | B2 | 1/2005 | Kline |
| 6,852,094 | B2 | 2/2005 | Beck |
| 6,852,104 | B2 | 2/2005 | Blomquist |
| 6,854,338 | B2 | 2/2005 | Khuri-Yakub et al. |
| 6,857,318 | B1 | 2/2005 | Silber et al. |
| 6,869,425 | B2 | 3/2005 | Briggs et al. |
| 6,873,268 | B2 | 3/2005 | Lebel et al. |
| 6,883,376 | B2 | 4/2005 | He |
| 6,885,881 | B2 | 4/2005 | Leonhardt |
| 6,887,216 | B2 | 5/2005 | Hochman et al. |
| 6,898,301 | B2 | 5/2005 | Iwanaga |
| 6,907,361 | B2 | 6/2005 | Molenaar |
| 6,907,792 | B2 | 6/2005 | Ohnishi |
| 6,915,170 | B2 | 7/2005 | Engleson et al. |
| 6,920,795 | B2 | 7/2005 | Bischoff et al. |
| 6,923,763 | B1 | 8/2005 | Kovatchev et al. |
| 6,928,338 | B1 | 8/2005 | Buchser et al. |
| 6,929,619 | B2 | 8/2005 | Fago et al. |
| 6,929,751 | B2 | 8/2005 | Bowman |
| 6,932,114 | B2 | 8/2005 | Sparks |
| 6,932,796 | B2 | 8/2005 | Sage et al. |
| 6,935,192 | B2 | 8/2005 | Sobek et al. |
| 6,936,029 | B2 | 8/2005 | Mann et al. |
| 6,941,005 | B2 | 9/2005 | Lary et al. |
| 6,942,636 | B2 | 9/2005 | Holst et al. |
| 6,945,954 | B2 | 9/2005 | Hochman et al. |
| 6,958,705 | B2 | 10/2005 | Lebel et al. |
| 6,964,204 | B2 | 11/2005 | Clark et al. |
| 6,973,374 | B2 | 12/2005 | Ader |
| 6,974,437 | B2 | 12/2005 | Lebel et al. |
| 6,975,922 | B2 | 12/2005 | Duncan et al. |
| 6,978,779 | B2 | 12/2005 | Haveri et al. |
| 6,979,326 | B2 | 12/2005 | Mann et al. |
| 6,981,960 | B2 | 1/2006 | Cho et al. |
| 6,984,218 | B2 | 1/2006 | Nayak et al. |
| 6,985,768 | B2 | 1/2006 | Hemming et al. |
| 6,985,870 | B2 | 1/2006 | Martucci et al. |
| 6,986,347 | B2 | 1/2006 | Hickle |
| 6,986,753 | B2 | 1/2006 | Bui |
| 6,997,905 | B2 | 2/2006 | Gillespie, Jr. et al. |
| 6,997,920 | B2 | 2/2006 | Mann et al. |
| 7,006,005 | B2 | 2/2006 | Nazarian et al. |
| 7,017,623 | B2 | 3/2006 | Tribble et al. |
| 7,021,148 | B2 | 4/2006 | Kuhn |
| 7,025,743 | B2 | 4/2006 | Mann et al. |
| 7,029,455 | B2 | 4/2006 | Flaherty |
| 7,029,456 | B2 | 4/2006 | Ware et al. |
| 7,031,857 | B2 | 4/2006 | Tarassenko et al. |
| 7,059,184 | B2 | 6/2006 | Kanouda et al. |
| 7,060,059 | B2 | 6/2006 | Keith et al. |
| 7,069,793 | B2 | 7/2006 | Ishikawa et al. |
| 7,072,725 | B2 | 7/2006 | Bristol et al. |
| 7,074,209 | B2 | 7/2006 | Evans et al. |
| 7,080,557 | B2 | 7/2006 | Adnan |
| 7,082,843 | B2 | 8/2006 | Clark et al. |
| 7,087,444 | B2 | 8/2006 | Wong et al. |
| 7,092,796 | B2 | 8/2006 | Vanderveen |
| 7,092,797 | B2 | 8/2006 | Gaines et al. |
| 7,093,502 | B2 | 8/2006 | Kupnik et al. |
| 7,096,729 | B2 | 8/2006 | Repko et al. |
| 7,103,419 | B2 | 9/2006 | Engleson et al. |
| 7,104,763 | B2 | 9/2006 | Bouton et al. |
| 7,104,769 | B2 | 9/2006 | Davis |
| 7,108,680 | B2 | 9/2006 | Rohr et al. |
| 7,109,878 | B2 | 9/2006 | Mann et al. |
| 7,115,113 | B2 | 10/2006 | Evans et al. |
| 7,117,041 | B2 | 10/2006 | Engleson et al. |
| 7,137,964 | B2 | 11/2006 | Flaherty |
| 7,141,037 | B2 | 11/2006 | Butterfield et al. |
| 7,152,490 | B1 | 12/2006 | Freund, Jr. et al. |
| 7,154,397 | B2 | 12/2006 | Zerhusen et al. |
| 7,161,488 | B2 | 1/2007 | Frasch |
| 7,162,290 | B1 | 1/2007 | Levin |
| 7,162,927 | B1 | 1/2007 | Selvan et al. |
| 7,171,277 | B2 | 1/2007 | Engleson et al. |
| 7,171,992 | B2 | 2/2007 | DiGianfilippo et al. |
| 7,174,789 | B2 | 2/2007 | Orr et al. |
| 7,185,288 | B2 | 2/2007 | McKeever |
| 7,197,943 | B2 | 4/2007 | Lee et al. |
| 7,201,734 | B2 | 4/2007 | Hickle |
| 7,204,823 | B2 | 4/2007 | Estes et al. |
| 7,206,715 | B2 | 4/2007 | Vanderveen et al. |
| 7,213,009 | B2 | 5/2007 | Pestotnik |
| 7,220,240 | B2 | 5/2007 | Struys et al. |
| 7,229,430 | B2 | 6/2007 | Hickle et al. |
| 7,230,529 | B2 | 6/2007 | Ketcherside |
| 7,232,430 | B2 | 6/2007 | Carlisle |
| 7,238,164 | B2 | 7/2007 | Childers et al. |
| 7,247,154 | B2 | 7/2007 | Hickle |
| 7,253,779 | B2 | 8/2007 | Greer et al. |
| 7,254,425 | B2 | 8/2007 | Lowery et al. |
| 7,258,534 | B2 | 8/2007 | Fathallah et al. |
| 7,267,664 | B2 | 9/2007 | Rizzo |
| 7,267,665 | B2 | 9/2007 | Steil et al. |
| 7,272,529 | B2 | 9/2007 | Hogan et al. |

(56) References Cited

U.S. PATENT DOCUMENTS

| | | | |
|---|---|---|---|
| 7,278,983 | B2 | 10/2007 | Ireland et al. |
| 7,291,123 | B2 | 11/2007 | Baraldi et al. |
| 7,293,461 | B1 | 11/2007 | Gimdt |
| 7,294,109 | B2 | 11/2007 | Lovett et al. |
| 7,296,482 | B2 | 11/2007 | Schaffer et al. |
| 7,300,418 | B2 | 11/2007 | Zaleski |
| 7,305,883 | B2 | 12/2007 | Khuri-Yakub et al. |
| 7,327,273 | B2 | 2/2008 | Hung et al. |
| D563,986 | S | 3/2008 | Lettau |
| 7,338,470 | B2 | 3/2008 | Katz |
| 7,343,224 | B2 | 3/2008 | DiGianfilippo et al. |
| 7,347,836 | B2 | 3/2008 | Peterson et al. |
| 7,347,854 | B2 | 3/2008 | Shelton et al. |
| 7,354,420 | B2 | 4/2008 | Steil et al. |
| 7,356,382 | B2 | 4/2008 | Vanderveen |
| 7,360,999 | B2 | 4/2008 | Nelson et al. |
| 7,364,562 | B2 | 4/2008 | Braig et al. |
| 7,367,942 | B2 | 5/2008 | Grage et al. |
| 7,369,948 | B1 | 5/2008 | Ferenczi et al. |
| 7,384,410 | B2 | 6/2008 | Eggers et al. |
| 7,397,166 | B1 | 7/2008 | Morgan et al. |
| 7,398,183 | B2 | 7/2008 | Holland et al. |
| 7,399,277 | B2 | 7/2008 | Saidara et al. |
| 7,402,153 | B2 | 7/2008 | Steil et al. |
| 7,402,154 | B2 | 7/2008 | Mendez |
| 7,407,489 | B2 | 8/2008 | Mendez |
| 7,414,534 | B1 | 8/2008 | Kroll et al. |
| 7,415,895 | B2 | 8/2008 | Kurisaki et al. |
| 7,426,443 | B2 | 9/2008 | Simon |
| 7,430,675 | B2 | 9/2008 | Lee et al. |
| 7,447,566 | B2 | 11/2008 | Knauper et al. |
| 7,447,643 | B1 | 11/2008 | Olson |
| 7,452,190 | B2 | 11/2008 | Bouton et al. |
| 7,454,314 | B2 | 11/2008 | Holland et al. |
| 7,471,994 | B2 * | 12/2008 | Ford ..................... G16H 20/17 700/282 |
| 7,477,997 | B2 | 1/2009 | Kaplit |
| 7,482,818 | B2 | 1/2009 | Greenwald et al. |
| 7,483,756 | B2 | 1/2009 | Engleson et al. |
| 7,490,021 | B2 | 2/2009 | Holland et al. |
| 7,491,187 | B2 | 2/2009 | Van Den Berghe et al. |
| 7,503,903 | B2 | 3/2009 | Carlisle et al. |
| 7,517,332 | B2 | 4/2009 | Tonelli et al. |
| 7,523,401 | B1 | 4/2009 | Aldridge |
| D593,125 | S | 5/2009 | Danton |
| 7,545,075 | B2 | 6/2009 | Huang et al. |
| D596,195 | S | 7/2009 | Wall |
| 7,556,616 | B2 | 7/2009 | Fathallah et al. |
| 7,561,986 | B2 | 7/2009 | Vanderveen et al. |
| 7,571,024 | B2 | 8/2009 | Duncan et al. |
| 7,605,730 | B2 | 10/2009 | Tomioka et al. |
| 7,614,310 | B2 | 11/2009 | Konzelmann |
| 7,645,258 | B2 | 1/2010 | White et al. |
| 7,654,127 | B2 | 2/2010 | Krulevitch et al. |
| 7,657,443 | B2 | 2/2010 | Crass |
| 7,668,731 | B2 | 2/2010 | Martucci et al. |
| 7,678,048 | B1 | 3/2010 | Urbano et al. |
| 7,693,697 | B2 | 4/2010 | Westenskow et al. |
| 7,699,806 | B2 | 4/2010 | Ware et al. |
| 7,705,727 | B2 | 4/2010 | Pestotnik |
| D617,807 | S | 6/2010 | Christie |
| 7,726,179 | B2 | 6/2010 | Muller |
| D621,845 | S | 8/2010 | Anzures |
| 7,766,873 | B2 | 8/2010 | Moberg et al. |
| 7,775,126 | B2 | 8/2010 | Eckhardt |
| 7,775,127 | B2 | 8/2010 | Wade |
| 7,785,284 | B2 | 8/2010 | Baralsi et al. |
| 7,785,313 | B2 | 8/2010 | Mastrototaro |
| 7,786,909 | B2 | 8/2010 | Udupa et al. |
| 7,806,886 | B2 | 10/2010 | Kanderian, Jr. et al. |
| 7,826,981 | B2 | 11/2010 | Goode, Jr. et al. |
| 7,847,276 | B2 | 12/2010 | Carlisle |
| 7,860,583 | B2 | 12/2010 | Condurso et al. |
| 7,871,394 | B2 | 1/2011 | Halbert et al. |
| 7,876,443 | B2 | 1/2011 | Bernacki |
| 7,895,053 | B2 | 2/2011 | Holland et al. |
| 7,895,882 | B2 | 3/2011 | Carlisle |
| 7,896,834 | B2 | 3/2011 | Smisson, III |
| 7,896,842 | B2 | 3/2011 | Palmroos et al. |
| 7,905,710 | B2 | 3/2011 | Wang et al. |
| 7,933,780 | B2 | 4/2011 | de la Huerga |
| 7,938,817 | B2 | 5/2011 | Gelfand et al. |
| 7,945,452 | B2 | 5/2011 | Fathallah et al. |
| D642,195 | S | 7/2011 | Marks |
| 7,976,508 | B2 | 7/2011 | Hoag |
| 7,981,073 | B2 | 7/2011 | Mollstam |
| 7,981,082 | B2 | 7/2011 | Wang et al. |
| 7,998,134 | B2 | 8/2011 | Fangrow |
| 8,002,736 | B2 | 8/2011 | Patrick et al. |
| 8,034,020 | B2 | 10/2011 | Dewey |
| 8,038,593 | B2 | 10/2011 | Friedman et al. |
| 8,065,161 | B2 | 11/2011 | Howard et al. |
| 8,067,760 | B2 | 11/2011 | Carlisle |
| 8,075,514 | B2 | 12/2011 | Butterfield et al. |
| 8,075,546 | B2 | 12/2011 | Carlisle et al. |
| 8,078,983 | B2 | 12/2011 | Davis et al. |
| 8,121,857 | B2 | 2/2012 | Galasso et al. |
| 8,149,131 | B2 | 4/2012 | Blomquist |
| D659,709 | S | 5/2012 | Eby |
| 8,175,668 | B1 | 5/2012 | Nabutovsky et al. |
| 8,177,739 | B2 | 5/2012 | Cartledge et al. |
| 8,180,440 | B2 | 5/2012 | McCombie et al. |
| 8,185,322 | B2 | 5/2012 | Schroeder et al. |
| 8,197,444 | B1 | 6/2012 | Bazargan et al. |
| 8,219,413 | B2 | 7/2012 | Martinez et al. |
| 8,221,395 | B2 | 7/2012 | Shelton et al. |
| 8,226,597 | B2 | 7/2012 | Jacobson et al. |
| 8,231,578 | B2 | 7/2012 | Fathallah et al. |
| 8,234,128 | B2 | 7/2012 | Martucci et al. |
| D667,452 | S | 9/2012 | Wujcik |
| D667,840 | S | 9/2012 | Anzures |
| 8,271,106 | B2 | 9/2012 | Wehba et al. |
| 8,287,514 | B2 | 10/2012 | Miller et al. |
| 8,291,337 | B2 | 10/2012 | Gannin et al. |
| 8,313,308 | B2 | 11/2012 | Lawless et al. |
| 8,317,698 | B2 | 11/2012 | Lowery |
| 8,317,750 | B2 | 11/2012 | Ware et al. |
| 8,317,752 | B2 | 11/2012 | Cozmi et al. |
| 8,318,094 | B1 | 11/2012 | Bayandorian et al. |
| 8,340,792 | B2 | 12/2012 | Condurso et al. |
| 8,347,731 | B2 | 1/2013 | Genosar |
| 8,359,338 | B2 | 1/2013 | Butterfield et al. |
| 8,361,021 | B2 | 1/2013 | Wang et al. |
| 8,378,837 | B2 | 2/2013 | Wang et al. |
| 8,388,598 | B2 | 3/2013 | Steinkogler |
| 8,398,616 | B2 | 3/2013 | Budiman |
| 8,403,908 | B2 | 3/2013 | Jacobson et al. |
| D679,727 | S | 4/2013 | Abratowski |
| 8,409,164 | B2 | 4/2013 | Fangrow |
| 8,449,524 | B2 | 5/2013 | Braig et al. |
| 8,469,942 | B2 | 6/2013 | Kow et al. |
| 8,477,307 | B1 | 7/2013 | Yufa et al. |
| 8,494,879 | B2 | 7/2013 | Davis et al. |
| 8,504,179 | B2 | 8/2013 | Blomquist |
| 8,506,552 | B2 | 8/2013 | Rebours |
| 8,517,990 | B2 | 8/2013 | Teel et al. |
| 8,518,021 | B2 | 8/2013 | Stewart et al. |
| 8,522,832 | B2 | 9/2013 | Lopez et al. |
| 8,523,797 | B2 | 9/2013 | Lowery et al. |
| 8,539,812 | B2 | 9/2013 | Stringham et al. |
| 8,543,416 | B2 | 9/2013 | Palmroos et al. |
| 8,577,692 | B2 | 11/2013 | Silkaitis et al. |
| 8,622,990 | B2 | 1/2014 | Estes et al. |
| 8,630,722 | B2 | 1/2014 | Condurso et al. |
| 8,665,214 | B2 | 3/2014 | Forutanpour et al. |
| 8,666,769 | B2 | 3/2014 | Butler et al. |
| 8,700,421 | B2 | 4/2014 | Feng et al. |
| 8,706,233 | B2 | 4/2014 | Su et al. |
| D705,260 | S | 5/2014 | Gerssen |
| 8,721,584 | B2 | 5/2014 | Braithwaite et al. |
| 8,728,020 | B2 | 5/2014 | Caleffi et al. |
| D706,294 | S | 6/2014 | Jewitt |
| 8,758,306 | B2 | 6/2014 | Lopez et al. |
| 8,761,906 | B2 | 6/2014 | Condurso et al. |

(56) References Cited

U.S. PATENT DOCUMENTS

| | | | | |
|---|---|---|---|---|
| D709,091 | S | 7/2014 | Kwon | |
| 8,768,719 | B2 | 7/2014 | Wehba et al. | |
| 8,771,251 | B2 | 7/2014 | Ruchti et al. | |
| 8,792,981 | B2 | 7/2014 | Yudovsky et al. | |
| D711,916 | S | 8/2014 | Matas | |
| D712,926 | S | 9/2014 | Meegan | |
| D713,417 | S | 9/2014 | Daniel | |
| D713,418 | S | 9/2014 | Yang | |
| D713,420 | S | 9/2014 | Dallmeyer | |
| 8,821,432 | B2 | 9/2014 | Unverdorben | |
| 8,823,382 | B2 | 9/2014 | Rondoni et al. | |
| 8,823,528 | B2 * | 9/2014 | Blomquist | A61M 5/142 340/539.12 |
| 8,857,269 | B2 | 10/2014 | Johnson et al. | |
| 8,858,185 | B2 | 10/2014 | Johnson et al. | |
| 8,905,965 | B2 | 12/2014 | Mandro et al. | |
| D721,385 | S | 1/2015 | Barling | |
| 8,948,734 | B2 | 2/2015 | Vaglio | |
| 8,964,185 | B1 | 2/2015 | Luo et al. | |
| 9,005,150 | B2 | 4/2015 | Ware et al. | |
| 9,026,370 | B2 | 5/2015 | Rubalcaba et al. | |
| 9,084,855 | B2 | 7/2015 | Ware et al. | |
| 9,114,217 | B2 | 8/2015 | Sur et al. | |
| 9,134,735 | B2 | 9/2015 | Lowery et al. | |
| 9,134,736 | B2 | 9/2015 | Lowery et al. | |
| 9,138,526 | B2 | 9/2015 | Ware et al. | |
| D742,413 | S | 11/2015 | Torres | |
| D742,414 | S | 11/2015 | Brunner | |
| D742,415 | S | 11/2015 | Cahill | |
| D743,414 | S | 11/2015 | Uno | |
| 9,190,010 | B2 | 11/2015 | Vik et al. | |
| D747,339 | S | 1/2016 | Cohen | |
| 9,240,002 | B2 | 1/2016 | Hume et al. | |
| D750,099 | S | 2/2016 | Kadosh | |
| 9,272,089 | B2 | 3/2016 | Jacobson et al. | |
| 9,316,216 | B1 | 4/2016 | Cook et al. | |
| D757,099 | S | 5/2016 | Seo | |
| 9,333,291 | B2 | 5/2016 | Jacobson et al. | |
| D758,379 | S | 6/2016 | Kadosh | |
| D759,036 | S | 6/2016 | Evanes | |
| D760,238 | S | 6/2016 | Suarez | |
| D760,248 | S | 6/2016 | Smith | |
| D760,295 | S | 6/2016 | Smith | |
| D760,788 | S | 7/2016 | Cho | |
| D761,820 | S | 7/2016 | Lee | |
| D762,238 | S | 7/2016 | Day | |
| 9,381,296 | B2 | 7/2016 | Arrizza et al. | |
| 9,393,362 | B2 | 7/2016 | Cozmi et al. | |
| D764,538 | S | 8/2016 | Lee | |
| 9,468,718 | B2 | 10/2016 | Hung et al. | |
| 9,498,583 | B2 | 11/2016 | Sur et al. | |
| D773,519 | S | 12/2016 | Hurley | |
| D777,205 | S | 1/2017 | Orr | |
| 9,545,475 | B2 | 1/2017 | Borges et al. | |
| 9,545,476 | B2 | 1/2017 | Qi et al. | |
| D779,537 | S | 2/2017 | Wingate-Whyte | |
| D781,874 | S | 3/2017 | Dunn | |
| D782,535 | S | 3/2017 | Menz | |
| 9,707,341 | B2 | 7/2017 | Dumas, III et al. | |
| 9,764,087 | B2 | 9/2017 | Peterfreund et al. | |
| 9,773,330 | B1 | 9/2017 | Douglas | |
| D803,881 | S | 11/2017 | Hurley | |
| D806,109 | S | 12/2017 | Day | |
| 9,852,265 | B1 | 12/2017 | Treacy et al. | |
| D809,006 | S | 1/2018 | Mehta | |
| 9,883,987 | B2 | 2/2018 | Lopez et al. | |
| 9,943,269 | B2 | 4/2018 | Muhsin et al. | |
| 9,995,611 | B2 | 6/2018 | Ruchti et al. | |
| 10,002,496 | B2 | 6/2018 | Humphrey | |
| 10,022,498 | B2 | 7/2018 | Ruchti et al. | |
| 10,046,112 | B2 | 8/2018 | Oruklu et al. | |
| D827,665 | S | 9/2018 | Segars | |
| 10,089,055 | B1 | 10/2018 | Fryman | |
| 10,099,009 | B1 | 10/2018 | Anderson et al. | |
| 10,166,328 | B2 | 1/2019 | Oruklu et al. | |
| 10,241,626 | B2 | 3/2019 | Miyazawa | |
| 10,297,350 | B2 | 5/2019 | Duke et al. | |
| 10,342,917 | B2 | 7/2019 | Shubinsky et al. | |
| 10,430,761 | B2 | 10/2019 | Hume et al. | |
| D865,777 | S | 11/2019 | Kovács | |
| 10,463,788 | B2 | 11/2019 | Day | |
| 10,549,248 | B2 | 2/2020 | Brown et al. | |
| 10,578,474 | B2 | 3/2020 | Ruchti et al. | |
| 10,596,316 | B2 | 3/2020 | Dumas, III et al. | |
| 10,635,784 | B2 | 4/2020 | Rubalcaba, Jr. et al. | |
| 10,656,894 | B2 | 5/2020 | Fryman | |
| 10,682,102 | B2 | 6/2020 | Declerck | |
| 10,709,885 | B2 | 7/2020 | Janders et al. | |
| D898,055 | S | 10/2020 | Connolly | |
| 10,850,024 | B2 | 12/2020 | Day et al. | |
| 10,874,793 | B2 | 12/2020 | Oruklu et al. | |
| 11,004,035 | B2 | 5/2021 | Hume et al. | |
| 11,007,119 | B2 | 5/2021 | Lopez et al. | |
| D922,432 | S | 6/2021 | Kataoka et al. | |
| D923,050 | S | 6/2021 | Kataoka et al. | |
| 11,029,911 | B2 | 6/2021 | Fryman | |
| D926,201 | S | 7/2021 | Bryant et al. | |
| D926,224 | S | 7/2021 | Hummel | |
| D928,813 | S | 8/2021 | Nurutdinov et al. | |
| D928,840 | S | 8/2021 | Amit et al. | |
| 11,090,431 | B2 | 8/2021 | Dumas, III et al. | |
| D931,884 | S | 9/2021 | Bryant et al. | |
| D931,892 | S | 9/2021 | Nurutdinov | |
| D934,282 | S | 10/2021 | Clymer | |
| 11,135,360 | B1 | 10/2021 | Jacobson et al. | |
| 11,219,715 | B2 | 1/2022 | Gray et al. | |
| 11,246,985 | B2 | 2/2022 | Gylland et al. | |
| D946,608 | S | 3/2022 | Higuchi | |
| 11,278,671 | B2 | 3/2022 | Cavendish, Jr. et al. | |
| 11,298,456 | B2 | 4/2022 | Shubinsky et al. | |
| 11,324,888 | B2 | 5/2022 | Shubinsky et al. | |
| 11,344,668 | B2 | 5/2022 | Sileika et al. | |
| 11,344,673 | B2 * | 5/2022 | Lindo | A61M 5/16827 |
| 11,376,361 | B2 | 7/2022 | Ruchti et al. | |
| 11,378,430 | B2 | 7/2022 | Ruchti et al. | |
| 11,395,875 | B2 | 7/2022 | Rubalcaba, Jr. et al. | |
| 11,433,177 | B2 | 9/2022 | Oruklu et al. | |
| 11,439,570 | B2 | 9/2022 | Lopez et al. | |
| 11,596,737 | B2 | 3/2023 | Dumas, III et al. | |
| 11,599,854 | B2 | 3/2023 | Hume et al. | |
| 11,623,042 | B2 | 4/2023 | Day | |
| 11,868,161 | B2 | 1/2024 | Fryman | |
| 11,883,361 | B2 | 1/2024 | Janssen | |
| D1,017,633 | S | 3/2024 | Chung | |
| D1,018,593 | S | 3/2024 | Chiah | |
| 11,933,650 | B2 | 3/2024 | Ruchti et al. | |
| D1,021,917 | S | 4/2024 | Ceniceroz | |
| D1,023,027 | S | 4/2024 | Slettnes | |
| D1,024,096 | S | 4/2024 | Zhong | |
| 11,972,395 | B2 | 4/2024 | Hume et al. | |
| D1,027,974 | S | 5/2024 | Correy | |
| 12,048,831 | B2 | 7/2024 | Oruklu et al. | |
| 12,059,551 | B2 | 8/2024 | Dumas, III et al. | |
| 12,076,531 | B2 | 9/2024 | Shubinsky et al. | |
| 12,083,310 | B2 | 9/2024 | Shubinsky et al. | |
| 12,115,337 | B2 | 10/2024 | Day et al. | |
| 12,201,811 | B2 | 1/2025 | Gylland et al. | |
| 12,310,921 | B2 | 5/2025 | Janssen | |
| 2001/0007636 | A1 | 7/2001 | Butterfield | |
| 2001/0014769 | A1 | 8/2001 | Bufe et al. | |
| 2001/0015099 | A1 | 8/2001 | Blaine | |
| 2001/0016056 | A1 | 8/2001 | Westphal et al. | |
| 2001/0032099 | A1 | 10/2001 | Joao | |
| 2001/0037060 | A1 | 11/2001 | Thompson et al. | |
| 2001/0041869 | A1 | 11/2001 | Causey et al. | |
| 2001/0044731 | A1 | 11/2001 | Coffman et al. | |
| 2002/0003892 | A1 | 1/2002 | Iwanaga | |
| 2002/0007116 | A1 | 1/2002 | Zatezalo et al. | |
| 2002/0013545 | A1 | 1/2002 | Soltanpour et al. | |
| 2002/0013551 | A1 | 1/2002 | Zaitsu et al. | |
| 2002/0015018 | A1 | 2/2002 | Shimazu et al. | |
| 2002/0018720 | A1 | 2/2002 | Carlisle et al. | |
| 2002/0029776 | A1 | 3/2002 | Blomquist | |
| 2002/0031838 | A1 | 3/2002 | Meinhart et al. | |

(56) References Cited

U.S. PATENT DOCUMENTS

| | | | |
|---|---|---|---|
| 2002/0032583 | A1 | 3/2002 | Joao |
| 2002/0040208 | A1 | 4/2002 | Flaherty et al. |
| 2002/0044059 | A1 | 4/2002 | Reeder et al. |
| 2002/0045806 | A1 | 4/2002 | Baker, Jr. et al. |
| 2002/0077852 | A1 | 6/2002 | Ford et al. |
| 2002/0082728 | A1 | 6/2002 | Mueller et al. |
| 2002/0083771 | A1 | 7/2002 | Khuri-Yakub et al. |
| 2002/0085952 | A1 | 7/2002 | Ellingboe et al. |
| 2002/0087115 | A1 | 7/2002 | Hartlaub |
| 2002/0093641 | A1 | 7/2002 | Ortyn et al. |
| 2002/0095486 | A1 | 7/2002 | Bahl |
| 2002/0099282 | A1 | 7/2002 | Knobbe et al. |
| 2002/0099334 | A1 | 7/2002 | Hanson et al. |
| 2002/0143580 | A1 | 10/2002 | Bristol et al. |
| 2002/0147389 | A1 | 10/2002 | Cavallaro et al. |
| 2002/0152239 | A1 | 10/2002 | Bautista-Lloyd et al. |
| 2002/0158919 | A1 | 10/2002 | Nacey |
| 2002/0168278 | A1 | 11/2002 | Jeon et al. |
| 2002/0173703 | A1 | 11/2002 | Lebel et al. |
| 2002/0183693 | A1 | 12/2002 | Peterson et al. |
| 2003/0009244 | A1 | 1/2003 | Engleson |
| 2003/0013959 | A1 | 1/2003 | Grunwald et al. |
| 2003/0018289 | A1 | 1/2003 | Ng et al. |
| 2003/0018308 | A1 | 1/2003 | Tsai |
| 2003/0025602 | A1 | 2/2003 | Medema et al. |
| 2003/0028082 | A1 | 2/2003 | Thompson |
| 2003/0030001 | A1 | 2/2003 | Cooper et al. |
| 2003/0045840 | A1 | 3/2003 | Burko |
| 2003/0050621 | A1 | 3/2003 | Lebel et al. |
| 2003/0060688 | A1 | 3/2003 | Ciarniello et al. |
| 2003/0060765 | A1 | 3/2003 | Campbell et al. |
| 2003/0065537 | A1 | 4/2003 | Evans |
| 2003/0065589 | A1 | 4/2003 | Giacchetti |
| 2003/0073954 | A1 | 4/2003 | Moberg et al. |
| 2003/0079746 | A1 | 5/2003 | Hickle |
| 2003/0083583 | A1 | 5/2003 | Kovtun et al. |
| 2003/0091442 | A1 | 5/2003 | Bush et al. |
| 2003/0104982 | A1 | 6/2003 | Wittmann et al. |
| 2003/0106553 | A1 | 6/2003 | Vanderveen |
| 2003/0117296 | A1 | 6/2003 | Seely |
| 2003/0125662 | A1 | 7/2003 | Bui |
| 2003/0130616 | A1 | 7/2003 | Steil |
| 2003/0135087 | A1 | 7/2003 | Hickle et al. |
| 2003/0136193 | A1 | 7/2003 | Fujimoto |
| 2003/0139701 | A1 | 7/2003 | White et al. |
| 2003/0140928 | A1 | 7/2003 | Bui et al. |
| 2003/0140929 | A1 | 7/2003 | Wilkes et al. |
| 2003/0141981 | A1 | 7/2003 | Bui et al. |
| 2003/0143746 | A1 | 7/2003 | Sage, Jr. |
| 2003/0144878 | A1 | 7/2003 | Wilkes et al. |
| 2003/0158508 | A1 | 8/2003 | DiGianfilippo |
| 2003/0159741 | A1 | 8/2003 | Sparks |
| 2003/0160683 | A1 | 8/2003 | Blomquist |
| 2003/0163789 | A1 | 8/2003 | Blomquist |
| 2003/0173408 | A1 | 9/2003 | Mosher, Jr. et al. |
| 2003/0186833 | A1 | 10/2003 | Huff et al. |
| 2003/0187338 | A1 | 10/2003 | Say et al. |
| 2003/0200116 | A1 | 10/2003 | Forrester |
| 2003/0204274 | A1 | 10/2003 | Ullestad et al. |
| 2003/0204416 | A1 | 10/2003 | Acharya |
| 2003/0212364 | A1 | 11/2003 | Mann et al. |
| 2003/0212379 | A1 | 11/2003 | Bylund et al. |
| 2003/0216682 | A1 | 11/2003 | Junker |
| 2003/0217962 | A1 | 11/2003 | Childers et al. |
| 2003/0233071 | A1 | 12/2003 | Gillespie, Jr. et al. |
| 2004/0030277 | A1 | 2/2004 | O'Mahony et al. |
| 2004/0047736 | A1 | 3/2004 | Nose et al. |
| 2004/0057226 | A1 | 3/2004 | Berthou et al. |
| 2004/0064342 | A1 | 4/2004 | Browne et al. |
| 2004/0073125 | A1 | 4/2004 | Lovett et al. |
| 2004/0073161 | A1 | 4/2004 | Tachibana |
| 2004/0077996 | A1 | 4/2004 | Jasperson et al. |
| 2004/0082908 | A1 | 4/2004 | Whitehurst |
| 2004/0082918 | A1 | 4/2004 | Evans et al. |
| 2004/0104271 | A1 | 6/2004 | Martucci et al. |

| | | | |
|---|---|---|---|
| 2004/0119753 | A1 | 6/2004 | Zencke |
| 2004/0120825 | A1 | 6/2004 | Bouton et al. |
| 2004/0128162 | A1 | 7/2004 | Schlotterbeck et al. |
| 2004/0128163 | A1 | 7/2004 | Goodman et al. |
| 2004/0130573 | A1 | 7/2004 | Konuma |
| 2004/0133166 | A1 | 7/2004 | Moberg et al. |
| 2004/0145114 | A1 | 7/2004 | Ippolito et al. |
| 2004/0147034 | A1 | 7/2004 | Gore et al. |
| 2004/0149823 | A1 | 8/2004 | Aptekar |
| 2004/0152970 | A1 | 8/2004 | Hunter et al. |
| 2004/0158193 | A1 | 8/2004 | Bui et al. |
| 2004/0167464 | A1 | 8/2004 | Ireland et al. |
| 2004/0167465 | A1 | 8/2004 | Kohler |
| 2004/0167804 | A1 | 8/2004 | Simpson |
| 2004/0172222 | A1 | 9/2004 | Simpson et al. |
| 2004/0172283 | A1 | 9/2004 | Vanderveen |
| 2004/0172289 | A1 | 9/2004 | Kozic et al. |
| 2004/0172301 | A1 | 9/2004 | Mihai et al. |
| 2004/0172302 | A1 | 9/2004 | Martucci et al. |
| 2004/0176984 | A1 | 9/2004 | White et al. |
| 2004/0181314 | A1 | 9/2004 | Zaleski |
| 2004/0193025 | A1 | 9/2004 | Steil et al. |
| 2004/0193325 | A1 | 9/2004 | Bonderud |
| 2004/0193328 | A1 | 9/2004 | Butterfield et al. |
| 2004/0193453 | A1 | 9/2004 | Butterfield et al. |
| 2004/0204638 | A1 | 10/2004 | Diab et al. |
| 2004/0204673 | A1 | 10/2004 | Flaherty et al. |
| 2004/0220517 | A1 | 11/2004 | Starkweather et al. |
| 2004/0225252 | A1 | 11/2004 | Gillespie et al. |
| 2004/0225409 | A1 | 11/2004 | Duncan et al. |
| 2004/0232219 | A1 | 11/2004 | Fowler |
| 2004/0247445 | A1 | 12/2004 | Nelson et al. |
| 2004/0253123 | A1 | 12/2004 | Xie et al. |
| 2004/0254434 | A1 | 12/2004 | Goodnow et al. |
| 2004/0254513 | A1 | 12/2004 | Shang et al. |
| 2005/0021006 | A1 | 1/2005 | Tonnies |
| 2005/0021297 | A1 | 1/2005 | Hartlaub |
| 2005/0022274 | A1 | 1/2005 | Campbell et al. |
| 2005/0038680 | A1 | 2/2005 | McMahon |
| 2005/0055242 | A1 | 3/2005 | Bello et al. |
| 2005/0055244 | A1 | 3/2005 | Mullan et al. |
| 2005/0065465 | A1 | 3/2005 | Lebel et al. |
| 2005/0075544 | A1 | 4/2005 | Shapiro et al. |
| 2005/0096593 | A1 | 5/2005 | Pope et al. |
| 2005/0099624 | A1 | 5/2005 | Staehr |
| 2005/0107923 | A1 | 5/2005 | Vanderveen |
| 2005/0108057 | A1 | 5/2005 | Cohen et al. |
| 2005/0119597 | A1 | 6/2005 | O'Mahony et al. |
| 2005/0119914 | A1 | 6/2005 | Batch |
| 2005/0131739 | A1 | 6/2005 | Rabinowitz et al. |
| 2005/0137522 | A1 | 6/2005 | Aoki |
| 2005/0143864 | A1 | 6/2005 | Blomquist |
| 2005/0145010 | A1 | 7/2005 | Vanderveen et al. |
| 2005/0171503 | A1 | 8/2005 | Van Den Berghe et al. |
| 2005/0171815 | A1 | 8/2005 | Vanderveen |
| 2005/0177045 | A1 | 8/2005 | Degertekin et al. |
| 2005/0177096 | A1 | 8/2005 | Bollish et al. |
| 2005/0182306 | A1 | 8/2005 | Sloan |
| 2005/0182355 | A1 | 8/2005 | Bui |
| 2005/0182366 | A1 | 8/2005 | Vogt et al. |
| 2005/0187515 | A1 | 8/2005 | Varrichio et al. |
| 2005/0192529 | A1 | 9/2005 | Butterfield et al. |
| 2005/0192557 | A1 | 9/2005 | Brauker et al. |
| 2005/0197554 | A1 | 9/2005 | Polcha |
| 2005/0197621 | A1 | 9/2005 | Poulsen et al. |
| 2005/0209563 | A1 | 9/2005 | Hopping et al. |
| 2005/0209793 | A1 | 9/2005 | Yamada |
| 2005/0224083 | A1 | 10/2005 | Crass |
| 2005/0235732 | A1 | 10/2005 | Rush |
| 2005/0238506 | A1 | 10/2005 | Mescher et al. |
| 2005/0240305 | A1 | 10/2005 | Bogash et al. |
| 2005/0273059 | A1 | 12/2005 | Mernoe et al. |
| 2005/0277890 | A1 | 12/2005 | Stewart et al. |
| 2005/0279419 | A1 | 12/2005 | Tribble et al. |
| 2006/0002799 | A1 | 1/2006 | Schann et al. |
| 2006/0009727 | A1 | 1/2006 | O'Mahony et al. |
| 2006/0009734 | A1 | 1/2006 | Martin |
| 2006/0042633 | A1 | 3/2006 | Bishop et al. |
| 2006/0047270 | A1 | 3/2006 | Shelton |

(56) References Cited

U.S. PATENT DOCUMENTS

2006/0053036 A1 3/2006 Coffman et al.
2006/0064020 A1 3/2006 Burnes et al.
2006/0064053 A1 3/2006 Bollish et al.
2006/0079768 A1 4/2006 Small et al.
2006/0079831 A1 4/2006 Gilbert
2006/0100746 A1 5/2006 Leibner-Druska
2006/0100907 A1 5/2006 Holland et al.
2006/0106649 A1 5/2006 Eggers et al.
2006/0116639 A1 6/2006 Russell
2006/0117856 A1 6/2006 Orr et al.
2006/0117867 A1 6/2006 Froehlich et al.
2006/0122867 A1 6/2006 Eggers et al.
2006/0135939 A1 6/2006 Brown
2006/0135940 A1 6/2006 Joshi
2006/0136095 A1 6/2006 Rob et al.
2006/0136271 A1 6/2006 Eggers et al.
2006/0140798 A1 6/2006 Kutsuzawa
2006/0143051 A1 6/2006 Eggers et al.
2006/0173260 A1 8/2006 Gaoni et al.
2006/0173406 A1 8/2006 Hayes et al.
2006/0181695 A1 8/2006 Sage, Jr.
2006/0187069 A1 8/2006 Duan
2006/0190302 A1 8/2006 Eggers et al.
2006/0195022 A1 8/2006 Trepagnier et al.
2006/0200007 A1 9/2006 Brockway et al.
2006/0200369 A1 9/2006 Batch et al.
2006/0211404 A1 9/2006 Cromp et al.
2006/0224140 A1 10/2006 Junker
2006/0224141 A1 10/2006 Rush et al.
2006/0224181 A1 10/2006 McEwen et al.
2006/0226088 A1 10/2006 Robinson et al.
2006/0226089 A1 10/2006 Robinson et al.
2006/0226090 A1 10/2006 Robinson et al.
2006/0229557 A1 10/2006 Fathallah et al.
2006/0229918 A1 10/2006 Fotsch et al.
2006/0235353 A1 10/2006 Gelfand et al.
2006/0255149 A1 11/2006 Retter et al.
2006/0258985 A1 11/2006 Russell
2006/0260416 A1 11/2006 Sage et al.
2006/0264895 A1 11/2006 Flanders
2006/0265246 A1 11/2006 Hoag
2006/0266128 A1 11/2006 Clark et al.
2006/0270971 A1 11/2006 Gelfand et al.
2006/0271286 A1 11/2006 Rosenberg
2006/0272421 A1 12/2006 Frinak et al.
2006/0275142 A1 12/2006 Bouton et al.
2007/0015972 A1 1/2007 Wang et al.
2007/0036511 A1 2/2007 Lundquist et al.
2007/0060796 A1 3/2007 Kim
2007/0060869 A1 3/2007 Tolle et al.
2007/0060871 A1 3/2007 Istoc
2007/0060872 A1 3/2007 Hall et al.
2007/0060874 A1 3/2007 Nesbitt et al.
2007/0062250 A1 3/2007 Krulevitch et al.
2007/0065363 A1 3/2007 Dalal et al.
2007/0078314 A1 4/2007 Grounsell
2007/0083152 A1 4/2007 Williams, Jr. et al.
2007/0084286 A1 4/2007 Ajay et al.
2007/0084288 A1 4/2007 Thomas et al.
2007/0088271 A1 4/2007 Richards
2007/0088333 A1 4/2007 Levin et al.
2007/0093753 A1 4/2007 Krulevitcvh et al.
2007/0094045 A1 4/2007 Cobbs et al.
2007/0094046 A1 4/2007 Cobbs et al.
2007/0100222 A1 5/2007 Mastrototaro et al.
2007/0100665 A1 5/2007 Brown
2007/0112298 A1 5/2007 Mueller et al.
2007/0118405 A1 5/2007 Campbell et al.
2007/0129618 A1 6/2007 Goldberger et al.
2007/0142822 A1 6/2007 Remde
2007/0156452 A1 7/2007 Batch
2007/0156456 A1 7/2007 McGillin et al.
2007/0179436 A1 8/2007 Braig et al.
2007/0180916 A1 8/2007 Tian et al.
2007/0191770 A1 8/2007 Moberg et al.
2007/0191817 A1 8/2007 Martin
2007/0197963 A1 8/2007 Griffiths et al.
2007/0214003 A1 9/2007 Holland et al.
2007/0215545 A1 9/2007 Bissler et al.
2007/0233035 A1 10/2007 Wehba et al.
2007/0233049 A1 10/2007 Wehba et al.
2007/0240497 A1 10/2007 Robinson et al.
2007/0250339 A1 10/2007 Mallett et al.
2007/0255250 A1 11/2007 Moberg et al.
2007/0257788 A1 11/2007 Carlson
2007/0267945 A1 11/2007 Sudol
2007/0270747 A1 11/2007 Remde
2007/0274843 A1 11/2007 Vanderveen et al.
2007/0289384 A1 12/2007 Sakai et al.
2008/0009684 A1 1/2008 Corsetti et al.
2008/0028868 A1 2/2008 Konzelmann et al.
2008/0033361 A1 2/2008 Evans et al.
2008/0039777 A1 2/2008 Katz et al.
2008/0048211 A1 2/2008 Khuri-Yakub et al.
2008/0058773 A1 3/2008 John
2008/0060448 A1 3/2008 Wiest et al.
2008/0065420 A1 3/2008 Tirinato et al.
2008/0071210 A1 3/2008 Moubayed et al.
2008/0071496 A1 3/2008 Glascock
2008/0071580 A1 3/2008 Marcus et al.
2008/0077116 A1 3/2008 Dailey et al.
2008/0086087 A1 4/2008 Spohn et al.
2008/0091466 A1 4/2008 Butler et al.
2008/0097288 A1 4/2008 Levin et al.
2008/0097289 A1 4/2008 Steil et al.
2008/0097317 A1 4/2008 Alholm et al.
2008/0098798 A1 5/2008 Riley et al.
2008/0119822 A1 5/2008 Knauper
2008/0125701 A1 5/2008 Moberg et al.
2008/0139907 A1 6/2008 Rao et al.
2008/0145249 A1 6/2008 Smisson
2008/0169044 A1 7/2008 Osborne et al.
2008/0172030 A1 7/2008 Blomquist et al.
2008/0177254 A1 7/2008 Shelton et al.
2008/0184784 A1 8/2008 Dam
2008/0188789 A1 8/2008 Galavotti et al.
2008/0188796 A1 8/2008 Steil et al.
2008/0200870 A1 8/2008 Palmroos et al.
2008/0208484 A1 8/2008 Butterfield et al.
2008/0214919 A1 9/2008 Harmon et al.
2008/0221521 A1 9/2008 Getz et al.
2008/0221522 A1 9/2008 Moberg et al.
2008/0243055 A1 10/2008 Fathallah et al.
2008/0262469 A1 10/2008 Bristol et al.
2008/0269663 A1 10/2008 Arnold et al.
2008/0269714 A1 10/2008 Mastrototaro et al.
2008/0269723 A1 10/2008 Mastrototaro et al.
2008/0275384 A1 11/2008 Mastrototaro et al.
2008/0300572 A1 12/2008 Rankers et al.
2009/0001908 A1 1/2009 Shubinsky et al.
2009/0005703 A1 1/2009 Fasciano
2009/0006061 A1 1/2009 Thukral et al.
2009/0006129 A1 1/2009 Thukral
2009/0006133 A1 1/2009 Weinert
2009/0015824 A1 1/2009 Shubinsky et al.
2009/0043171 A1 2/2009 Rule
2009/0053071 A1 2/2009 Wang et al.
2009/0054743 A1 2/2009 Stewart
2009/0054754 A1 2/2009 McMahon et al.
2009/0062727 A1 3/2009 Woo
2009/0069743 A1 3/2009 Krishnamoorthy et al.
2009/0077248 A1 3/2009 Castellucci et al.
2009/0082676 A1 3/2009 Bennison
2009/0088731 A1 4/2009 Campbell et al.
2009/0097029 A1 4/2009 Tokhtuev et al.
2009/0099866 A1 4/2009 Newman
2009/0105636 A1 4/2009 Hayter et al.
2009/0112155 A1 4/2009 Zhao
2009/0114037 A1 5/2009 Smith
2009/0119330 A1 5/2009 Sampath et al.
2009/0124963 A1 5/2009 Hogard et al.
2009/0124964 A1 5/2009 Leach et al.
2009/0126825 A1 5/2009 Eliuk et al.
2009/0131861 A1 5/2009 Braig et al.

(56) References Cited

U.S. PATENT DOCUMENTS

| | | | |
|---|---|---|---|
| 2009/0135196 A1 | 5/2009 | Holland et al. | |
| 2009/0143726 A1 | 6/2009 | Bouton et al. | |
| 2009/0144025 A1 | 6/2009 | Bouton et al. | |
| 2009/0144026 A1 | 6/2009 | Bouton et al. | |
| 2009/0149743 A1 | 6/2009 | Barron et al. | |
| 2009/0153058 A1 | 6/2009 | Feng et al. | |
| 2009/0156922 A1 | 6/2009 | Goldberger et al. | |
| 2009/0156975 A1 | 6/2009 | Robinson et al. | |
| 2009/0177146 A1 | 7/2009 | Nesbitt et al. | |
| 2009/0177188 A1 | 7/2009 | Steinkogler | |
| 2009/0177248 A1 | 7/2009 | Roberts | |
| 2009/0177769 A1 | 7/2009 | Roberts | |
| 2009/0177992 A1 | 7/2009 | Rubalcaba et al. | |
| 2009/0178485 A1 | 7/2009 | Thomas et al. | |
| 2009/0183147 A1 | 7/2009 | Davis et al. | |
| 2009/0192367 A1 | 7/2009 | Braig et al. | |
| 2009/0198347 A1 | 8/2009 | Kirzinger | |
| 2009/0205426 A1 | 8/2009 | Balschat et al. | |
| 2009/0209938 A1 | 8/2009 | Aalto-Setala | |
| 2009/0209945 A1 | 8/2009 | Lobl et al. | |
| 2009/0212966 A1 | 8/2009 | Panduro | |
| 2009/0221890 A1 | 9/2009 | Saffer et al. | |
| 2009/0223294 A1 | 9/2009 | Thomas et al. | |
| 2009/0227939 A1 | 9/2009 | Memoe et al. | |
| 2009/0264720 A1 | 10/2009 | Torjman et al. | |
| 2009/0270810 A1 | 10/2009 | DeBelser | |
| 2009/0270833 A1 | 10/2009 | DeBelser | |
| 2009/0281497 A1* | 11/2009 | Kamen | A61M 5/14248 604/151 |
| 2009/0299156 A1 | 12/2009 | Simpson et al. | |
| 2010/0022988 A1 | 1/2010 | Wochner | |
| 2010/0036310 A1 | 2/2010 | Hillman | |
| 2010/0056992 A1 | 3/2010 | Hayter | |
| 2010/0057042 A1 | 3/2010 | Hayter | |
| 2010/0069892 A1 | 3/2010 | Steinbach et al. | |
| 2010/0077866 A1 | 4/2010 | Graboi et al. | |
| 2010/0079760 A1 | 4/2010 | Bernacki | |
| 2010/0094251 A1 | 4/2010 | Estes et al. | |
| 2010/0106082 A1 | 4/2010 | Zhou | |
| 2010/0114027 A1 | 5/2010 | Jacobson et al. | |
| 2010/0121170 A1 | 5/2010 | Rule | |
| 2010/0121415 A1 | 5/2010 | Skelton et al. | |
| 2010/0130933 A1 | 5/2010 | Holland et al. | |
| 2010/0131434 A1 | 5/2010 | Magent et al. | |
| 2010/0141460 A1 | 6/2010 | Tokhtuev et al. | |
| 2010/0147081 A1 | 6/2010 | Thomas et al. | |
| 2010/0152554 A1 | 6/2010 | Steine et al. | |
| 2010/0160854 A1 | 6/2010 | Gauthier | |
| 2010/0168535 A1 | 7/2010 | Robinson et al. | |
| 2010/0177375 A1 | 7/2010 | Seyfried | |
| 2010/0185142 A1 | 7/2010 | Kamen et al. | |
| 2010/0185182 A1 | 7/2010 | Alme et al. | |
| 2010/0198034 A1 | 8/2010 | Thomas et al. | |
| 2010/0198182 A1 | 8/2010 | Lanigan et al. | |
| 2010/0198183 A1 | 8/2010 | Lanigan et al. | |
| 2010/0211002 A1 | 8/2010 | Davis | |
| 2010/0212407 A1 | 8/2010 | Stringham et al. | |
| 2010/0212675 A1 | 8/2010 | Walling et al. | |
| 2010/0214110 A1 | 8/2010 | Wang et al. | |
| 2010/0217154 A1 | 8/2010 | Deshmukh et al. | |
| 2010/0217621 A1 | 8/2010 | Schoenberg | |
| 2010/0271218 A1 | 10/2010 | Hoag et al. | |
| 2010/0271479 A1 | 10/2010 | Heydlauf | |
| 2010/0273738 A1 | 10/2010 | Valcke et al. | |
| 2010/0280430 A1 | 11/2010 | Caleffi et al. | |
| 2010/0292634 A1 | 11/2010 | Kircher | |
| 2010/0295686 A1 | 11/2010 | Sloan et al. | |
| 2010/0298765 A1 | 11/2010 | Budiman et al. | |
| 2010/0312039 A1 | 12/2010 | Quirico et al. | |
| 2010/0317093 A1 | 12/2010 | Turewicz et al. | |
| 2010/0317952 A1 | 12/2010 | Budiman et al. | |
| 2010/0318025 A1 | 12/2010 | John | |
| 2011/0000560 A1 | 1/2011 | Miller et al. | |
| 2011/0001605 A1 | 1/2011 | Kiani et al. | |
| 2011/0004186 A1 | 1/2011 | Butterfield | |
| 2011/0009797 A1 | 1/2011 | Kelly et al. | |
| 2011/0028885 A1 | 2/2011 | Eggers et al. | |
| 2011/0040247 A1 | 2/2011 | Mandro et al. | |
| 2011/0046558 A1 | 2/2011 | Gravesen et al. | |
| 2011/0054311 A1 | 3/2011 | Williams et al. | |
| 2011/0062703 A1 | 3/2011 | Lopez et al. | |
| 2011/0064612 A1 | 3/2011 | Franzoni et al. | |
| 2011/0071464 A1 | 3/2011 | Palerm | |
| 2011/0071844 A1 | 3/2011 | Cannon et al. | |
| 2011/0072379 A1 | 3/2011 | Gannon | |
| 2011/0077480 A1 | 3/2011 | Bloom et al. | |
| 2011/0078608 A1 | 3/2011 | Gannon et al. | |
| 2011/0099313 A1 | 4/2011 | Bolanowski | |
| 2011/0105983 A1 | 5/2011 | Kelly et al. | |
| 2011/0106561 A1 | 5/2011 | Eaton, Jr. et al. | |
| 2011/0107251 A1 | 5/2011 | Guaitoli et al. | |
| 2011/0137241 A1 | 6/2011 | DelCastillo et al. | |
| 2011/0144595 A1 | 6/2011 | Cheng | |
| 2011/0152770 A1 | 6/2011 | Diperna et al. | |
| 2011/0160649 A1 | 6/2011 | Pan | |
| 2011/0162647 A1 | 7/2011 | Huby et al. | |
| 2011/0172918 A1 | 7/2011 | Tome | |
| 2011/0175728 A1 | 7/2011 | Baker, Jr. | |
| 2011/0184379 A1 | 7/2011 | Van Antwerp et al. | |
| 2011/0190598 A1 | 8/2011 | Shusterman | |
| 2011/0190694 A1 | 8/2011 | Lanier et al. | |
| 2011/0218514 A1 | 9/2011 | Rebours | |
| 2011/0238032 A1 | 9/2011 | McTaggart et al. | |
| 2011/0264006 A1 | 10/2011 | Ali et al. | |
| 2011/0264043 A1 | 10/2011 | Kotnick et al. | |
| 2011/0282321 A1 | 11/2011 | Steil et al. | |
| 2011/0313390 A1 | 12/2011 | Roy et al. | |
| 2011/0319728 A1 | 12/2011 | Petisce et al. | |
| 2011/0320049 A1 | 12/2011 | Chossat et al. | |
| 2012/0016215 A1 | 1/2012 | Condurso et al. | |
| 2012/0023431 A1 | 1/2012 | Roth | |
| 2012/0025995 A1 | 2/2012 | Moberg et al. | |
| 2012/0035535 A1 | 2/2012 | Johnson et al. | |
| 2012/0059234 A1 | 3/2012 | Barrett et al. | |
| 2012/0068001 A1 | 3/2012 | Pushkarsky et al. | |
| 2012/0083760 A1 | 4/2012 | Ledford et al. | |
| 2012/0085277 A1 | 4/2012 | Abdel-Rahman | |
| 2012/0089411 A1 | 4/2012 | Srnka et al. | |
| 2012/0095433 A1 | 4/2012 | Hungerford et al. | |
| 2012/0116195 A1 | 5/2012 | Chaum et al. | |
| 2012/0123322 A1 | 5/2012 | Scarpaci et al. | |
| 2012/0143116 A1 | 6/2012 | Ware et al. | |
| 2012/0180790 A1 | 7/2012 | Montgomery | |
| 2012/0185267 A1 | 7/2012 | Kamen et al. | |
| 2012/0191059 A1 | 7/2012 | Cummings et al. | |
| 2012/0194341 A1 | 8/2012 | Peichel et al. | |
| 2012/0203177 A1 | 8/2012 | Lanier | |
| 2012/0222774 A1 | 9/2012 | Husnu et al. | |
| 2012/0226350 A1 | 9/2012 | Rudser et al. | |
| 2012/0245525 A1 | 9/2012 | Pope et al. | |
| 2012/0259278 A1 | 10/2012 | Hayes et al. | |
| 2012/0310204 A1 | 12/2012 | Krogh et al. | |
| 2012/0323212 A1 | 12/2012 | Murphy | |
| 2013/0006666 A1 | 1/2013 | Schneider | |
| 2013/0009551 A1 | 1/2013 | Knapp | |
| 2013/0012880 A1 | 1/2013 | Blomquist | |
| 2013/0012917 A1 | 1/2013 | Miller et al. | |
| 2013/0032634 A1 | 2/2013 | McKirdy | |
| 2013/0041342 A1 | 2/2013 | Bernini et al. | |
| 2013/0044111 A1 | 2/2013 | VanGilder et al. | |
| 2013/0083191 A1 | 4/2013 | Lowery et al. | |
| 2013/0085443 A1 | 4/2013 | Lowery et al. | |
| 2013/0085689 A1 | 4/2013 | Sur et al. | |
| 2013/0110538 A1 | 5/2013 | Butterfield et al. | |
| 2013/0116649 A1 | 5/2013 | Breton et al. | |
| 2013/0150766 A1 | 6/2013 | Olde et al. | |
| 2013/0150821 A1 | 6/2013 | Bollish et al. | |
| 2013/0158504 A1 | 6/2013 | Ruchti et al. | |
| 2013/0173291 A1 | 7/2013 | Kelly | |
| 2013/0177455 A1 | 7/2013 | Kamen et al. | |
| 2013/0184676 A1 | 7/2013 | Kamen et al. | |
| 2013/0197930 A1 | 8/2013 | Garibaldi et al. | |
| 2013/0201482 A1 | 8/2013 | Munro | |
| 2013/0218080 A1 | 8/2013 | Peterfreund et al. | |

(56) References Cited

U.S. PATENT DOCUMENTS

| | | | |
|---|---|---|---|
| 2013/0253430 | A1 | 9/2013 | Kouyoumjian et al. |
| 2013/0253946 | A1 | 9/2013 | Broselow |
| 2013/0261993 | A1 | 10/2013 | Ruchti et al. |
| 2013/0274576 | A1 | 10/2013 | Amirouche et al. |
| 2013/0281965 | A1 | 10/2013 | Kamen et al. |
| 2013/0291116 | A1 | 10/2013 | Homer |
| 2013/0296823 | A1 | 11/2013 | Melker et al. |
| 2013/0296984 | A1 | 11/2013 | Burnett et al. |
| 2013/0318158 | A1 | 11/2013 | Teng et al. |
| 2013/0322201 | A1 | 12/2013 | Hitchcock et al. |
| 2013/0345658 | A1 | 12/2013 | Browne et al. |
| 2013/0345666 | A1 | 12/2013 | Panduro et al. |
| 2014/0039446 | A1 | 2/2014 | Day |
| 2014/0067425 | A1 | 3/2014 | Dudar et al. |
| 2014/0132524 | A1 | 5/2014 | Lee |
| 2014/0145915 | A1 | 5/2014 | Ribble et al. |
| 2014/0180711 | A1 | 6/2014 | Kamen et al. |
| 2014/0224829 | A1 | 8/2014 | Capone et al. |
| 2014/0267563 | A1 | 9/2014 | Baca et al. |
| 2014/0303754 | A1 | 10/2014 | Nixon et al. |
| 2014/0350513 | A1 | 11/2014 | Oruklu et al. |
| 2014/0358077 | A1 | 12/2014 | Oruklu et al. |
| 2015/0025453 | A1 | 1/2015 | Ledford et al. |
| 2015/0033073 | A1 | 1/2015 | Yang et al. |
| 2015/0051458 | A1 | 2/2015 | Chen |
| 2015/0057108 | A1 | 2/2015 | Regimbal |
| 2015/0065988 | A1 | 3/2015 | Holderle et al. |
| 2015/0089439 | A1 | 3/2015 | Wada |
| 2015/0114515 | A1 | 4/2015 | Phallen |
| 2015/0141921 | A1 | 5/2015 | Stewart et al. |
| 2015/0168958 | A1 | 6/2015 | Downie et al. |
| 2015/0246175 | A1 | 9/2015 | Shubinsky et al. |
| 2015/0265765 | A1 | 9/2015 | Yavorsky et al. |
| 2015/0278474 | A1 | 10/2015 | Stueckemann |
| 2015/0289823 | A1 | 10/2015 | Rack-Gomer et al. |
| 2015/0338340 | A1 | 11/2015 | Jiang et al. |
| 2015/0363086 | A1 | 12/2015 | Lim |
| 2015/0371004 | A1 | 12/2015 | Jones |
| 2016/0000998 | A1 | 1/2016 | Estes |
| 2016/0019352 | A1 | 1/2016 | Seo |
| 2016/0042264 | A1 | 2/2016 | Borges et al. |
| 2016/0051750 | A1 | 2/2016 | Tsoukalis |
| 2016/0103960 | A1 | 4/2016 | Hume et al. |
| 2016/0110088 | A1 | 4/2016 | Vik et al. |
| 2016/0144101 | A1 | 5/2016 | Pananen |
| 2016/0151560 | A1 | 6/2016 | Toro et al. |
| 2016/0151562 | A1 | 6/2016 | Magers et al. |
| 2016/0151601 | A1 | 6/2016 | Cardelius et al. |
| 2016/0158437 | A1 | 6/2016 | Biasi et al. |
| 2016/0175517 | A1 | 6/2016 | Sileika et al. |
| 2016/0193604 | A1 | 7/2016 | McFarland et al. |
| 2016/0253460 | A1 | 9/2016 | Kanada |
| 2016/0256622 | A1 | 9/2016 | Day et al. |
| 2016/0339167 | A1 | 11/2016 | Ledford et al. |
| 2017/0010677 | A1 | 1/2017 | Roh |
| 2017/0043089 | A1 | 2/2017 | Handler |
| 2017/0056604 | A1 | 3/2017 | Cowan |
| 2017/0068498 | A1 | 3/2017 | Hashem |
| 2017/0132867 | A1 | 5/2017 | Berg et al. |
| 2017/0354941 | A1 | 12/2017 | Brown et al. |
| 2018/0018440 | A1 | 1/2018 | Sugawara |
| 2018/0021514 | A1 | 1/2018 | Rosinko et al. |
| 2018/0028749 | A1 | 2/2018 | Dumas, III et al. |
| 2018/0206798 | A1 | 7/2018 | Murai |
| 2018/0296751 | A1 | 10/2018 | Lefort et al. |
| 2018/0300994 | A1 | 10/2018 | Nelson et al. |
| 2018/0326146 | A1 | 11/2018 | Gupta et al. |
| 2019/0072405 | A1 | 3/2019 | Luchner |
| 2019/0091401 | A1 | 3/2019 | Ruchti et al. |
| 2019/0111209 | A1 | 4/2019 | Murphy et al. |
| 2019/0117890 | A1 | 4/2019 | Oruklu et al. |
| 2019/0160254 | A1 | 5/2019 | Anand |
| 2019/0196770 | A1 | 6/2019 | Fryman |
| 2019/0201607 | A1 | 7/2019 | Öberg |
| 2019/0262535 | A1 | 8/2019 | Shubinsky et al. |
| 2019/0282757 | A1 | 9/2019 | Gylland et al. |
| 2019/0351131 | A1 | 11/2019 | Butterfield et al. |
| 2020/0054825 | A1 | 2/2020 | Kamen et al. |
| 2020/0069864 | A1 | 3/2020 | Shubinsky et al. |
| 2020/0113784 | A1 | 4/2020 | Lopez et al. |
| 2020/0330689 | A1 | 10/2020 | Nemoto et al. |
| 2020/0384191 | A1 | 12/2020 | Rosinko et al. |
| 2021/0158481 | A1 | 5/2021 | Wang |
| 2021/0158946 | A1 | 5/2021 | Starobinets et al. |
| 2021/0162115 | A1 | 6/2021 | Surine |
| 2021/0260283 | A1 | 8/2021 | Oruklu et al. |
| 2021/0304864 | A1 | 9/2021 | Kamen et al. |
| 2022/0088305 | A1 | 3/2022 | Cavendish, Jr. |
| 2022/0176037 | A1 | 6/2022 | Jacobson et al. |
| 2022/0184302 | A1 | 6/2022 | Cavendish, Jr. et al. |
| 2022/0184304 | A1 | 6/2022 | Rinehart |
| 2022/0296806 | A1 | 9/2022 | Shubinsky et al. |
| 2022/0305200 | A1 | 9/2022 | Gylland et al. |
| 2022/0331518 | A1 | 10/2022 | Shubinsky et al. |
| 2022/0401640 | A1 | 12/2022 | Jacobson |
| 2023/0010290 | A1 | 1/2023 | Oruklu et al. |
| 2023/0010638 | A1 | 1/2023 | Rubalcaba, Jr. et al. |
| 2023/0017117 | A1 | 1/2023 | Sileika et al. |
| 2023/0058662 | A1 | 2/2023 | Ruchti et al. |
| 2023/0112979 | A1 | 4/2023 | Xavier |
| 2023/0115595 | A1 | 4/2023 | Cousineau et al. |
| 2023/0181419 | A1 | 6/2023 | Fister |
| 2023/0245741 | A1 | 8/2023 | Shigyo |
| 2023/0270938 | A1 | 8/2023 | Dumas, III et al. |
| 2023/0285669 | A1 | 9/2023 | Day |
| 2023/0310735 | A1 | 10/2023 | Cousineau |
| 2024/0201922 | A1 | 6/2024 | Fryman |
| 2024/0263981 | A1 | 8/2024 | Ruchti et al. |
| 2024/0366858 | A1 | 11/2024 | Cousineau et al. |

FOREIGN PATENT DOCUMENTS

| | | |
|---|---|---|
| CA | 2 113 473 | 3/1993 |
| CA | 2 551 817 | 7/2005 |
| CA | 2 554 407 | 8/2005 |
| CN | 105682703 | 6/2016 |
| CN | 107106042 | 8/2017 |
| CN | 110573195 | 12/2019 |
| CN | 105848694 | 1/2020 |
| CN | 111954966 | 11/2020 |
| CN | 306893275 | 10/2021 |
| CN | 307412164 | 6/2022 |
| CN | 307979072 | 4/2023 |
| CN | 112105405 | 8/2023 |
| CN | 308499458 | 3/2024 |
| CO | 0020220004676-0001 | 11/2022 |
| CO | 0020220008155-0001 | 11/2022 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |

(56) References Cited

FOREIGN PATENT DOCUMENTS

| | | |
|---|---|---|
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| EP | 008932172-0003 | 4/2022 |
| EP | 008932172-0004 | 4/2022 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| GB | 6 201 192 | 4/2022 |
| GB | 6 201 193 | 4/2022 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| TW | 201841165 | 11/2018 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/010029 | 3/1999 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 01/033710 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/061745 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2006/026270 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/026420 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/028524 | 2/2013 |
| WO | WO 2013/036854 | 3/2013 |

(56) References Cited

FOREIGN PATENT DOCUMENTS

| | | |
|---|---|---|
| WO | WO 2013/096769 | 6/2013 |
| WO | WO 2014/004216 | 1/2014 |
| WO | WO 2015/134478 | 9/2015 |
| WO | WO 2016/160321 | 10/2016 |
| WO | WO 2017/051271 | 3/2017 |
| WO | WO 2017/087157 | 5/2017 |
| WO | WO 2017/144366 | 8/2017 |
| WO | WO 2017/197024 | 11/2017 |
| WO | WO 2019/063462 | 4/2019 |
| WO | WO 2019/092680 | 5/2019 |
| WO | WO 2020/214717 | 10/2020 |
| WO | WO 2022/020184 | 1/2022 |
| WO | WO 2022/072159 | 4/2022 |
| WO | WO 2022/125471 | 6/2022 |
| WO | WO 2023/064662 | 4/2023 |
| WO | WO 2023/108030 | 6/2023 |
| WO | WO 2023/192791 | 10/2023 |
| WO | WO 2023/244922 | 12/2023 |

OTHER PUBLICATIONS

Daimiwal et al., "Wireless Transfusion Supervision and Analysis Using Embedded System", IEEE, 2010 International Conference ICBBT, China, Apr. 2010, pp. 56-60.
Junda, Lin, "Global development trends of green bonds", Jul. 10, 2018, pp. 9.
Notice of Opposition in European Patent Application No. 16759381.3 (Patent No. EP3285827), dated May 31, 2023 in 48 pages.
Response to Notice of Opposition in European Patent Application No. 16759381.3 (Patent No. EP3285827), dated Oct. 23, 2023 in 63 pages.
International Search Report and Written Opinion received in PCT Application No. PCT/US2015/033345, dated Sep. 14, 2015 in 11 pages.
International Preliminary Report on Patentability and Written Opinion received in PCT Application No. PCT/US2015/033345, dated Dec. 8, 2016 in 10 pages.
Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
Alaris® Medical Systems, "Signature Edition® GOLD—Single & Dual Channel Infusion System", San Diego, CA, USA, date unknown, but believed to be at least as early as Nov. 29, 2008, pp. 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. <http://web.archive.org/web/20160403140025/http://www.baxter.com/news-media/newsroom/press-releases/2014/05_08_14_sigma.page>.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, <https://store.cerner.com/items/7>.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", <https://web.archive.org/web/20090813092423/http://www.diffen.com/difference/Continually_vs_Continuously>, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. <http://archive.epo.org/epo/pubs/oj013/11_13/11_5033.pdf>.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. <http://archive.epo.org/epo/pubs/oj009/12_09/12_5829.pdf>.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", <http://www.merriam-webster.com/dictionary/froth>, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. <www.hospira.com/products_and_services/infusion_pumps/plum/index>.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.

(56) References Cited

OTHER PUBLICATIONS

Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", <https://www.elektronik.ropla.eu/pdf/stock/mcp/mta11200b.pdf>, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, <http://staff.ustc.edu.cn/~ketang/papers/TangSuganYaoQin_PR04.pdf>.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Amazon, Post-it Message "Sign Here" Flags, 30/Dispenser, 4 Dispensers/Pack, Published Sep. 29, 2016, https://www.amazon.com/Assorted-Color-Colors-Dispenser-MMM684SH/dp/B00006JNMN/?th=1, 2 pages.
File:Soldado, Raso Fuerza Aerea Boliviana.jpg, Feb. 9, 2021, https://commons.m.wikimedia.org/wiki/File:Soldado_Raso_Fuerza_A%C3%A9rea_Boliviana.jpg, 1 page.
Fresenius, "Infusion Workstation: Orchestra® Base Intensive", Operator's Guide, Jun. 20, 2006, <https://manualmachine.com/fresenius/orchestrabaseunit/7455278-user-manual/>, 24 pages.
"ICU Medical Receives FDA Clearance for New Infusion Pump", Medical Design & Development Staff, Aug. 29, 2023, https://www.medicaldesigndevelopment.com/topics/devices/news/22871498/icu-medical-receives-fda-clearance-for-new-infusion-pump, 2 pages.
Jusko: Moving from Basic Toward Systems Pharmacodynamic Models; Department of Pharmaceutical Sciences, School of Pharmacy and Pharmaceutical Sciences, State University of New York at Buffalo, Buffalo, New York 14214; Journal of Pharmaceutical Sciences, vol. 102, No. 9, Sep. 2013; DOI 10.1002/jps; in 11 pages.
Lesson 1: Introduction to Pharmacokinetics and Pharmacodynamics; Concepts in Clinical Pharmacokinetics; in 18 pages.
Meibohm, et al; Basic Concepts of Pharmacokinetic/pharmacodynamic (PK/PD) modelling; Department of Pharmaceutics, College of Pharmacy, University of Florida, Gainesville, FL, USA, International Journal of Clinical Pharmacology and Therapeutics, vol. 35, No. 10-1997 (401-413); 13 pages.
Safer Care Victoria: Dobutamine I Safer Care Victoria; https://www.safercare.vic.gov.au/clinical-guidance/critical/dobutamine; in 9 pages.
Safer Care Victoria: Dopamine I Safer Care Victoria; https://www.safercare.vic.gov.au/clinical-guidance/critical/dopamine; in 9 pages.
Safer Care Victoria: Adrenaline (epinephrine) I Safer Care Victoria; https://www.safercare.vic.gov.au/clinical-guidance/critical/adrenaline-epinephrine; in 9 pages.
Safer Care Victoria: Isoprenaline I Safer Care Victoria; https://www.safercare.vic.gov.au/clinical-guidance/critical/isoprenaline; in 8 pages.
Safer Care Victoria: Noradrenaline (norepinephrine) I Safer Care Victoria; https://www.safercare.vic.gov.au/clinical-guidance/critical/noradrenaline-norepinephrine; in 8 pages.
The heart.org Medscape: nitroglycerin IV (Rx); glyceryl trinitrate IV, IV Nitroglycerin (nitroglycerin IV) dosing, indication, interaction, adverse effects, and more; https://reference.medscape.com/drug/glyceryl-trinitrate-iv-iv-nitroglycerin-nitroglycerin-iv-342278#10; 1 page.

* cited by examiner

INFUSION SYSTEM AND PUMP WITH CONFIGURABLE CLOSED LOOP DELIVERY RATE CATCH-UP

TECHNICAL FIELD

The present invention relates to medical devices. More specifically, the invention relates to infusion systems and pumps with configurable closed loop delivery rate catch-up.

BACKGROUND OF THE INVENTION

Description of the Related Art

Infusion pumps are medical devices that deliver fluids, including nutrients and medications such as antibiotics, chemotherapy drugs, and pain relievers, into a patient's body in controlled amounts. Many types of pumps, including large volume, patient-controlled analgesia (PCA), elastomeric, syringe, enteral, and insulin pumps, are used worldwide in healthcare facilities such as hospitals, and in the home. Clinicians and patients rely on pumps for safe and accurate administration of fluids and medications.

Presently available infusion pumps use an open loop pumping rate: the desired pumping or volumetric flow rate is input directly, or calculated from an input volume to be infused and delivery period or duration, and the infusion pump operates at a single target motor speed or stroke frequency to deliver the desired pumping or flow rate regardless of external conditions. Unfortunately, flow delivery can be interrupted by a variety of conditions, such as a stoppage or pause based upon a full or partial occlusion, a kinked tube, an air-in-line alarm, hanging a new IV bag, vein clot, or the like. Once the flow delivery is interrupted, the time in which there is no medication delivery is lost, resulting in a delay in desired infusion completion.

Nurses typically work in shifts and expect certain medications to be started and/or finished within their shift and plan accordingly. When occlusions, pauses, or other disturbances interrupt or delay medication delivery, this disrupts the nurses' planning for patient care within their respective shifts. In addition, the patients in these scenarios would not receive the medicine required within the allotted time.

It would be desirable to have an infusion system and pump with configurable closed loop delivery rate catch-up that would overcome the above disadvantages.

SUMMARY OF THE INVENTION

One aspect of the present invention provides an infusion system with catch-up of interrupted delivery of an infusion programmable by a user, the infusion system including a medication management unit having a processing unit and a storage medium coupled to the processing unit, the storage medium containing programming code executable by the processing unit to: provide a graphical user interface for modifying a drug library of the medication management unit; receive a catch-up rate factor on the graphical user interface; update the drug library with the catch-up rate factor; and transmit the updated drug library to a memory of an infusion pump; and the infusion pump being in electronic communication with the medication management unit, having a processor and the memory being coupled to the processor, the memory containing programming code executable by the processor to: receive the updated drug library at the medical device with the catch-up rate factor; receive a desired infusion rate from the user at the medical device; calculate an expected accumulated infusion volume as a function of time from the desired infusion rate; request delivery of the infusion at the desired infusion rate; determine an actual accumulated infusion volume at a particular time; increase the desired infusion rate by the catch-up rate factor to generate a catch-up infusion rate when at the particular time the actual accumulated infusion volume is less than the expected accumulated infusion volume; and request delivery of the infusion at the catch-up infusion rate.

Another aspect of the present invention provides an infusion pump with catch-up of interrupted delivery of an infusion programmable by a user, the infusion pump including a processor; a memory coupled to the processor, the memory containing programming code to: receive a desired infusion rate from the user at the medical device; calculate an expected accumulated infusion volume as a function of time from the desired infusion rate; request delivery of the infusion at the desired infusion rate; determine an actual accumulated infusion volume at a particular time; increase the desired infusion rate by a catch-up rate factor to generate a catch-up infusion rate when at the particular time the actual accumulated infusion volume is less than the expected accumulated infusion volume; and request delivery of the infusion at the catch-up infusion rate.

Yet another aspect of the present invention provides a method of catching-up interrupted delivery of an infusion from an infusion pump, the method including entering a desired infusion rate for the infusion pump; calculating an expected accumulated infusion volume as a function of time from the desired infusion rate; requesting the infusion pump to deliver the infusion at the desired infusion rate; determining an actual accumulated infusion volume at a particular time; increasing the (desired) infusion rate by a catch-up rate factor to generate a catch-up infusion rate when at the particular time the actual accumulated infusion volume is less than the expected accumulated infusion volume; and requesting the infusion pump to deliver the infusion at the catch-up infusion rate.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PREFERRED EMBODIMENT

Figure 1:
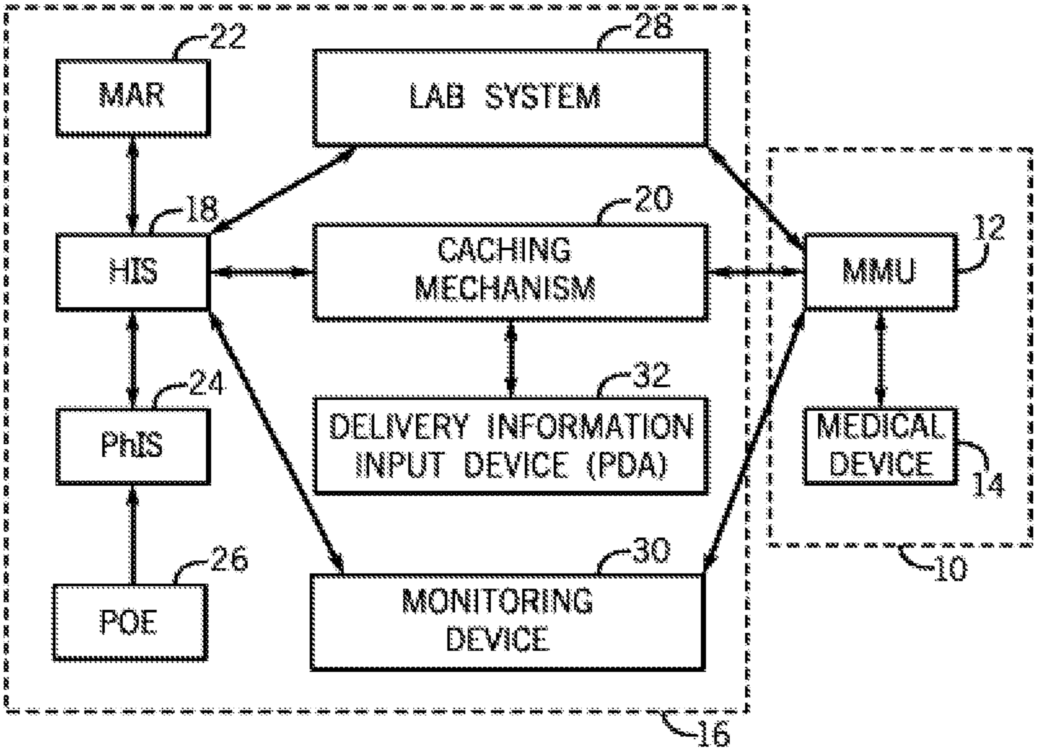
FIG. 1 is a schematic diagram of the medication management system including a medication management unit and a medical device integrated with other systems in a hospital environment, in accordance with the present invention.

FIG. 1 is a schematic diagram of the medication management system including a medication management unit and a medical device integrated with an information system, in accordance with the present invention. The medication management system (MMS) 10 includes a medication management unit (MMU) 12 and a medical device 14, typically operating in a hospital environment 16. The term hospital environment as defined herein is used broadly to mean any medical care facility, including but not limited to a hospital, treatment center, clinic, doctor's office, day surgery center, hospice, nursing home, and any of the above associated with a home care environment. There can be a variety of information systems in a hospital environment. As shown in FIG. 1, the MMU 12 communicates to a hospital information system (HIS) 18 via a caching mechanism 20 that is part of the hospital environment 16.

Those skilled in the art will appreciate that the caching mechanism 20 is primarily a pass through device for facilitating communication with the HIS 18 and its functions can be eliminated or incorporated into the MMU 12 (FIG. 1) and/or the medical device 14 and/or the HIS 18 and/or other information systems or components within the hospital environment 16. The caching mechanism 20 provides temporary storage of hospital information data separate from the HIS 18, the medication administration record system (MAR) 22, pharmacy information system (PhIS) 24, physician order entry (POE) 26, and/or Lab System 28. The caching mechanism 20 provides information storage accessible to the medication management system 10 to support scenarios where direct access to data within the hospital environment 16 is not available or not desired. In one example, the caching mechanism 20 provides continued flow of information in and out of the MMU 12 in instances where the HIS 18 is down or the connectivity between the MMU 12 and the electronic network (not shown) is down.

The HIS 18 communicates with a medication administration record system (MAR) 22 for maintaining medication records and a pharmacy information system (PhIS) 24 for delivering drug orders to the HIS. A physician/provider order entry (POE) device 26 permits a healthcare provider to deliver a medication order prescribed for a patient to the hospital information system directly or indirectly via the PhIS 24. One skilled in the art will also appreciate that a medication order can be sent to the MMU 12 directly from the PhIS 24 or POE device 26. As used herein, the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. As shown, the MMU 12 communicates directly to the lab system 28 and monitoring device 30. However, those skilled in the art will appreciate that the MMU 12 can communicate with the lab system 28 and monitoring device 30 indirectly via the HIS 18, the caching mechanism 20, the medical device 14 or some other intermediary device or system.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter, the delivery information input device 32 is referred to as input device 32. Alternatively, the machine readable indicia can be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or can be integrated wholly or in part with the medical device.

Figure 2:
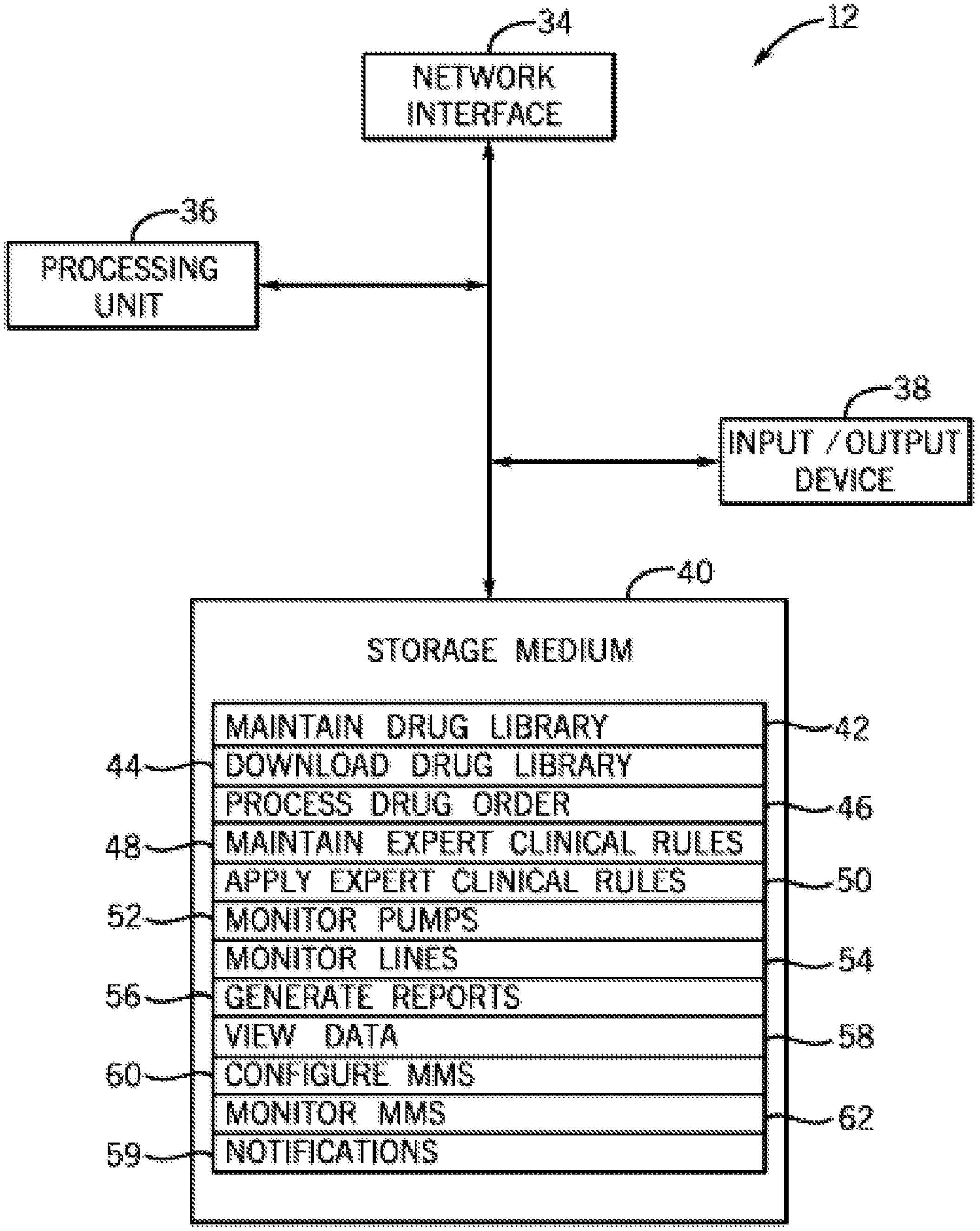
FIG. 2 is a schematic diagram of the medication management unit, in accordance with the present invention.

FIG. 2 is a schematic diagram of the medication management unit, in accordance with the present invention. The medication management unit 12 includes a network interface 34 for connecting the MMU 12 to multiple components of a hospital environment 16, one or more medical devices 14, and any other desired device or network. A processing unit 36 is included in MMU 12 and performs various operations described in greater detail below. A display/input or user interface device 38 communicates with the processing unit 36 and allows the user to receive output from processing unit 36 and/or input information into the processing unit 36. Those skilled in the art will appreciate that the display/input device 38 can be provided as a separate display device and a separate input device.

An electronic storage medium 40 communicates with the processing unit 36 and stores programming code and data necessary for the processing unit 36 to perform the functions of the MMU 12. More specifically, the storage medium 40 stores multiple programs formed in accordance with the present invention for various functions of the MMU 12 including but not limited to the following programs: Maintain Drug Library 42; Download Drug Library 44; Process Drug Order 46; Maintain Expert Clinical Rules 48; Apply Expert Clinical Rules 50; Monitor Pumps 52; Monitor Lines 54; Generate Reports 56; View Data 58; Configure the MMS 60; and Monitor the MMS 62. The Maintain Drug Library 42 program creates, updates, and deletes drug entries and establishes a current active drug library. The Download Drug Library 44 program updates medical devices 14 with the current drug library. The Process Drug Order 46 program processes the medication order for a patient, verifying that the point of care (POC) medication and delivery parameters match those ordered. The Maintain Expert Clinical Rules 48 program creates, updates, and deletes the rules that describe the hospital's therapy and protocol regimens. The Apply Expert Clinical Rules 50 program performs logic processing to ensure safety and considers other infusions or medication orders, patient demographics, and current patient conditions. The Monitor Pumps 52 program acquires ongoing updates of status events, and alarms transmitted both near real-time and in batch mode, as well as tracking the location, current assignment, and software versions such as the drug library version residing on medical device 14. The Monitor Lines 54 program acquires ongoing updates of status, events and alarms for each channel or line for a medical device 14 that supports multiple drug delivery channels or lines. The Generate Reports 56 program provides a mechanism that allows the user to generate various reports of the data held in the MMU storage medium 40. The View Data 58 program provides a mechanism that supports various display or view capabilities for users of the MMU 12. The Notifications 59 program provides a mechanism for scheduling and delivery of events to external systems and users. The Configure the MMS 60 program provides a mechanism for system administrators to install and configure the MMS 10. The Monitor the MMS 62 program enables information technology operations staff capabilities to see the current status of MMS 10 components and processing, and other aspects of day-to-day operations such as system start up, shut down, backup and restore.

Figure 3:
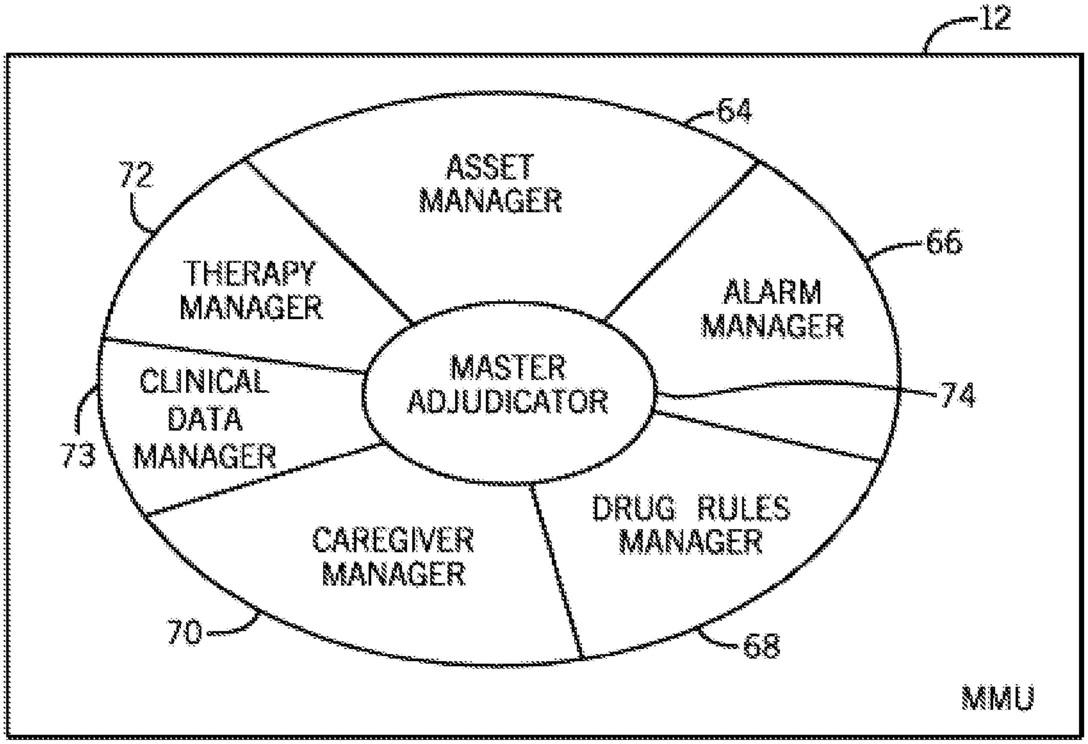
FIG. 3 is a schematic diagram of some of the major functions performed by the medication management unit, in accordance with the present invention.

FIG. 3 is a schematic diagram of some of the major functions performed by the medication management unit, in accordance with the present invention. The various functional programs 42-62 of the MMU 12, each including separate features and rules, are partitioned (at a higher level than shown in FIG. 2) and logically organized into interrelated managing units of the MMU 12. As shown, the MMU 12 includes an asset manager 64, an alarm manager 66, a drug library manager (such as, for example, is included in HOSPIRA MEDNET™ software) 68, a caregiver manager 70, a therapy manager 72, and/or a clinical data manager 73. However, those skilled in the art will appreciate that additional or alternative hospital system managing units can be provided without departing from the present invention. Additionally, the MMU 12 includes a master adjudicator 74 between the separate interrelated managing units 64-73 of the MMU 12, to regulate the interaction between the separate management units.

Further, while the MMU 12 as described herein appears as a single device, there can be more than one MMU 12 operating harmoniously and sharing the same database. For example the MMU 12 can consist of a collection of MMU specific applications running on distinct servers in order to avoid a single point of failure, address availability requirements, and handle a high volume of requests. In this example, each individual server portion of the MMU 12 operates in conjunction with other server portions of the MMU 12 to redirect service requests to another server portion of the MMU 12. Additionally, the master adjudicator 74 assigns redirected service requests to another server portion of the MMU 12, prioritizing each request and also ensuring that each request is processed.

With reference to FIGS. 2 & 3, the managing units 64-72 each include separate features and rules to govern their operation. For example, the asset manager 64 governs the execution of the Monitor Pumps 52 and Monitor Lines 54 programs; the drug library manager 68 governs the execution of the Drug Library 42 and Download Drug Library 44 programs; the therapy manager 72 governs the execution of the Process Drug Order 46, Maintain Expert Clinical Rules 48, and Apply Expert Clinical Rules 50 programs; and the clinical data manager 73 governs the execution of the Generate Reports 56 and View Data 58 programs. Other distribution of the functional MMU programs 42-62 among the managing units 64-73 can be made in accordance with the present invention.

Figure 4:
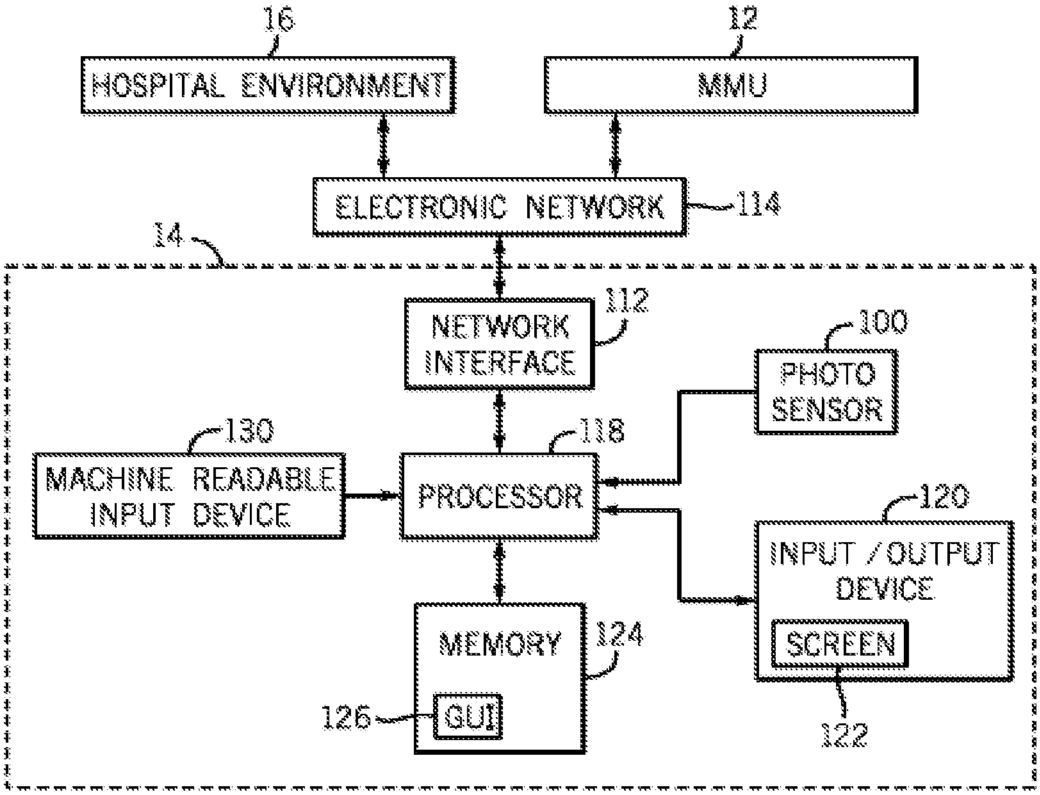
FIG. 4 is a schematic diagram of a medical device, in accordance with the present invention.

FIG. 4 is a schematic diagram of a medical device, in accordance with the present invention. An electronic network 114 connects the MMU 12, medical device 14, and hospital environment 16 for electronic communication. The electronic network 114 can be a completely wireless network, a completely hard wired network, or some combination thereof. As used herein, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic, testing or sampling device.

The pump style medical device 14 includes a network interface 112 for connecting the medical device 14 to electronic network 114. Where a wireless connection to the electronic network 114 is desired, network interface 112 operates an antenna for wireless connection to the electronic network 114. The antenna can project outside the medical device 14 or be enclosed within the housing of the device.

A processor 118 is included in the medical device 14, includes a real time clock (not shown), and performs various operations described in greater detail below. The input/output device 120 allows the user to receive output from the medical device 14 and/or input information into the medical device 14.

Those skilled in the art will appreciate that input/output device 120 can be provided as a single device such as a touch screen 122, or as a separate display device and a separate input device (not shown). In one embodiment, the display screen 122 of the medical device 14 is a thin film transistor active matrix color liquid crystal display with a multi-wire touch screen. A membrane generally impermeable to fluids overlays the display screen 122 so the user can press images of keys or buttons on the underlying screen with wet gloves, dry gloves, or without gloves to trigger an input.

A memory 124 communicates with the processor 118 and stores code and data necessary for the processor 118 to perform the functions of the medical device 14. More specifically, the memory 124 stores multiple programs formed in accordance with the present invention for various functions of the medical device 14 including a graphical user interface program 126 with multiple subparts described in greater detail below.

Figure 5A:
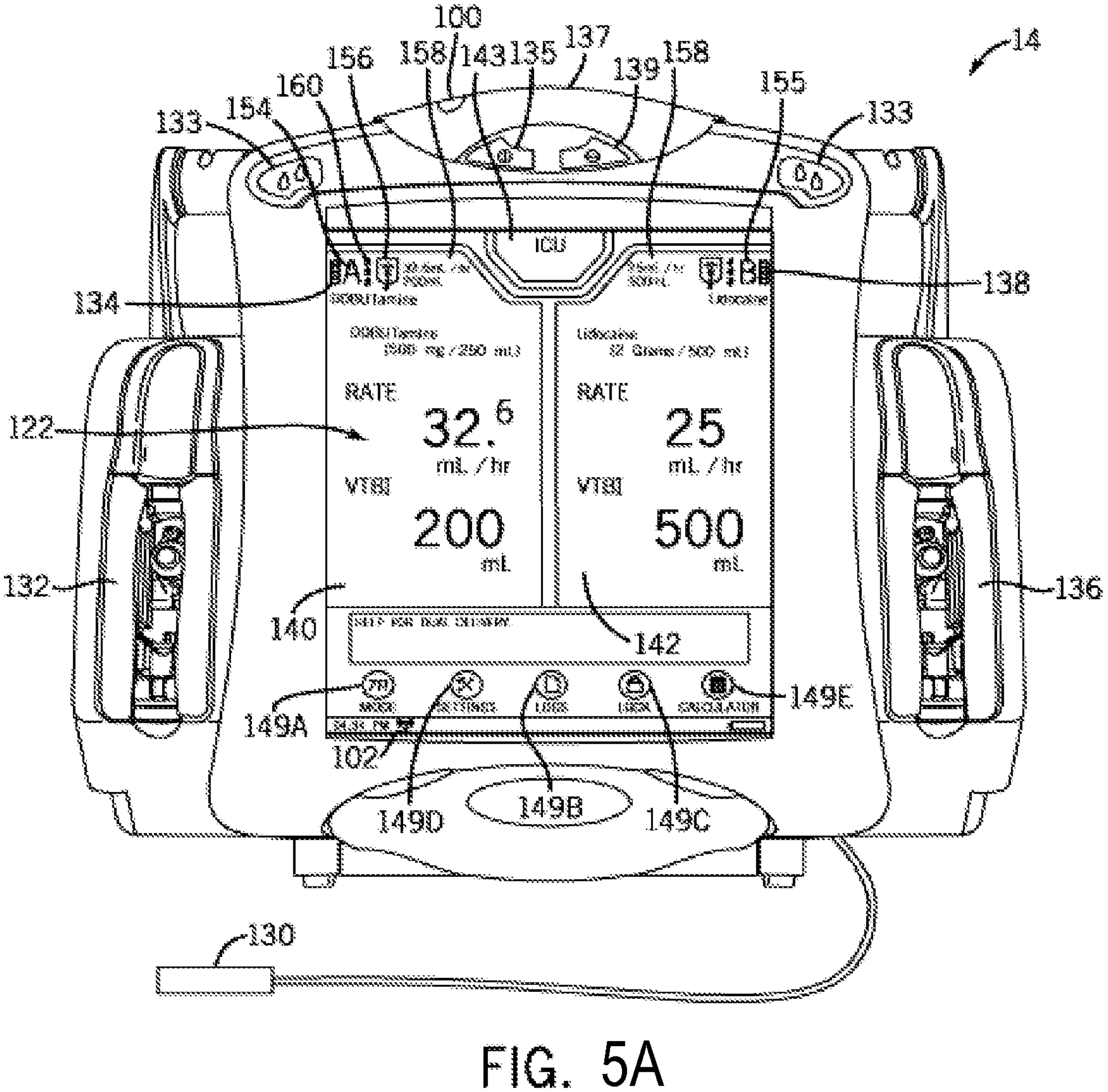
FIGS. 5A & 5B are perspective views of a multi-channel medical device, in accordance with the present invention.
Figure 5B:
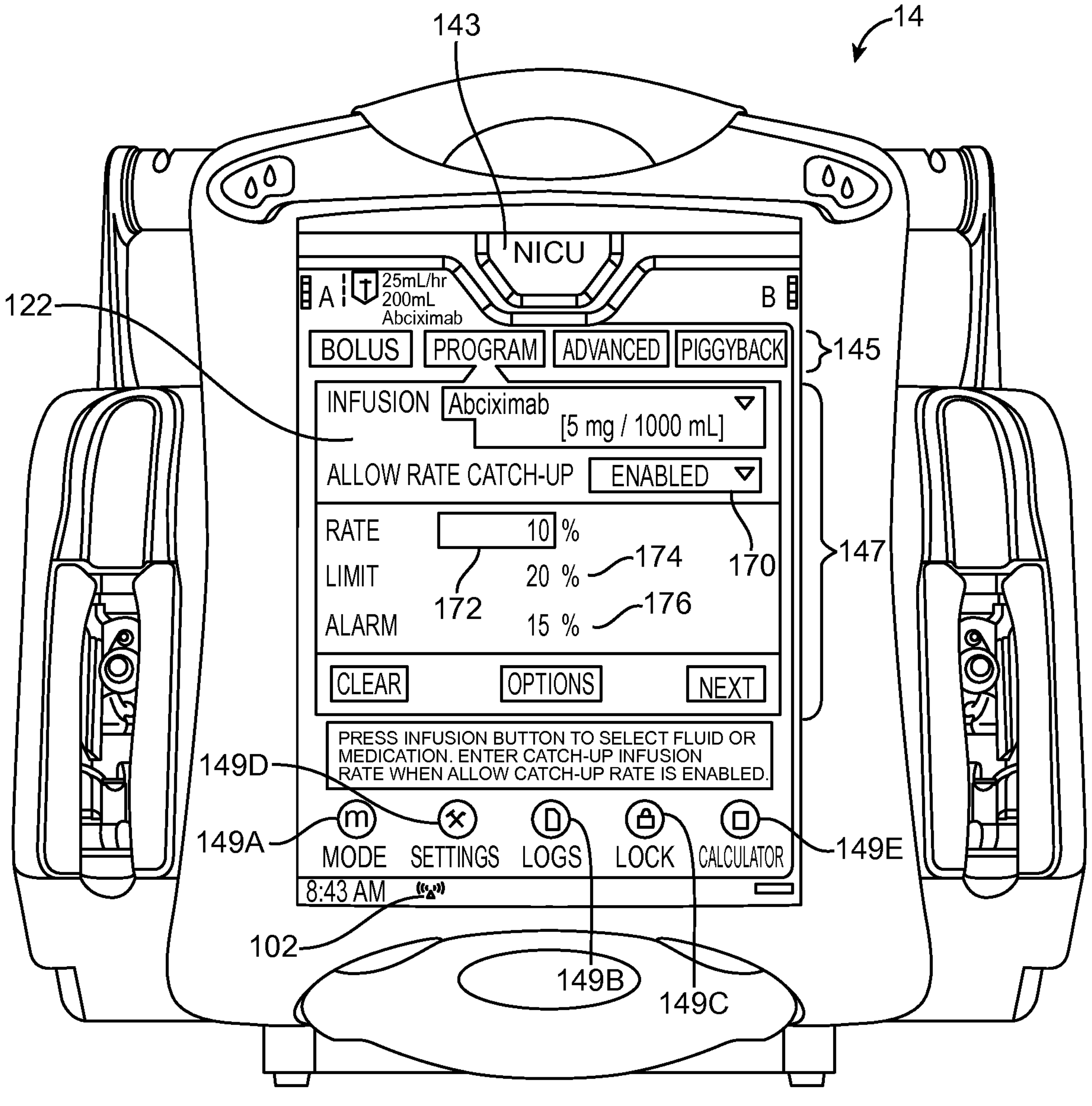

FIGS. 5A & 5B are perspective views of a multi-channel medical device in communication with a machine-readable input device, in accordance with the present invention. FIG. 5A illustrates an infusion pump with a split screen display, having one portion associated with each channel. FIG. 5B illustrates an infusion pump with a screen display for receiving infusion programmable input from a user. The medical device 14 in this example is a multi-channel infusion pump. Those skilled in the art will appreciate that the medical device 14 can be a single channel infusion pump, a multi-channel infusion pump (as shown), a combination thereof, or the like, as desired for a particular application.

Referring to FIG. 5A, the medical device 14 provides a machine-readable input device 130. The machine-readable input device 130 communicates with the medical device 14 to input machine-readable information to the medical device 14. The machine-readable input device 130 can communicate, directly or indirectly, with the medical device 14 via a wireless or hard-wired connection. The machine-readable input device 130 can be a device that is separate from but associated or in communication with the medical device 14. The machine-readable input device 130 can be any sort of data input means, including those adapted to read machine-readable indicia, such as a barcode scanner or handheld personal digital assistant (PDA). Alternatively, the machine-readable input device 130 can be operable to read in other known forms of machine-readable information, such as radio frequency identification tags (RFID), touch memory, digital photography, biometrics, etc.

The medical device 14 is a multi-channel pump having a first channel 132 with first channel machine-readable label 134 and a second channel 136 with a second channel machine-readable label 138. A user of the medical device 14 operates the machine-readable input device 130 to select a channel from one or more channels 132 and 136, by scanning in the associated machine-readable label 134 or 138.

The user selects the desired channel 132 or 136 by using the machine-readable input device 130 to scan a factory or hospital programmed, unique, machine-readable label 134 or 138 that is electronically generated and presented on the screen 122, preferably positioned near the respective channel 132 or 136. Alternatively, the machine-readable labels 134 and 138 are physically affixed to the medical device 14, preferably on or positioned near the channel 132 and 136, respectively. Since the machine-readable labels 134 and 138 are generated and/or can be stored in memory 124 by the medical device 14, the medical device 14 can associate the machine-readable labels 134 and 138 to the channels 132 or 136. The medical device 14 then allows the user to program and activate the selected channel 132 or 136. The user may also manually select the desired channel by touching an appropriate folder tab on the touch screen. The folder tabs are labeled and/or physically arranged on the screen so as to be proximate to the corresponding channel 132 or 136.

In a further aspect of the wireless embodiment, all the medical devices can periodically broadcast a unique wireless device/channel IP address and/or a self-generated unique machine-readable label (for example, a barcode) 134 or 138 that can also be presented on the screen 122. Alternatively, the machine-readable labels 134 and 138 are physically affixed to or posted on the medical device 14. Each medical device will correlate such broadcasted or posted device/channel IP addresses and/or barcodes with a particular patient, who is also identified by a unique machine readable label (not shown) or patient IP address. The user associates the desired pump(s) or channel(s) 132, 136 with the patient by using the machine-readable input device 130 to scan the unique machine-readable labels 134, 138 and the patient's machine readable label. This causes the appropriate pump processor(s) 118 to associate the appropriate pump channel(s) 132, 136 with the patient. Then the pumps or channels can associate, communicate, and coordinate with each other wirelessly.

The graphical user interface program reallocates screen 122 for the medical device 14. Specifically, FIG. 5A illustrates a multi-channel infusion medical device 14 with a split touch screen 122 having a first channel screen portion 140 associated with first channel 132 and a second channel screen portion 142 associated with the second channel 136. Each channel screen portion 140 and 142 presents a subset of the delivery information regarding the respective channels 132 or 136 including without limitation therapeutic agent name, concentration, dose rate, VTBI, and alarm information, in a font size that it is easily readable by a user from a distance such as, for example, from approximately fifteen to twenty feet (4.6-6.2 meters) away. This is what is defined herein as a "far view" delivery screen. The far view delivery screens display subsets of the information found on the relevant "near view" delivery screens. The near view delivery screen displays information such as, drug name, concentration, dose rate, time remaining, VTBI, volume remaining, and alarm name for the highest priority alarm if in an alarm state.

In practice, the delivery screen displays a near view when the user is programming the device as illustrated by FIG. 5B. The near view delivery screen will switch to the far view delivery screen after a predetermined period of time that is predetermined by the manufacturer, configurable by the facility via the drug library, and/or set by the caregiver at the pump, for example after 20 seconds. Often, the user does not want to wait for the predetermined length of time to view the far screen.

Returning to FIG. 5A, the channel screen portion 140 or 142 selected or corresponding to the tab selected expands in area but the size of at least some of the text therein is shrunk. The shrinkage of one of the channel screen portions 140 and 142 and enlargement of its counterpart provides additional space for one or more data display or data entry fields to be placed on screen 122, as shown in FIG. 5B. As discussed below, data displays or data entry fields are placed on screen 122 in space previously occupied by portions of the channel screen portion 140 or 142. This reallocation of space on screen 122 permits the user to enter inputs more easily since the data entry field can be large, preferably at least as large or, more preferably, larger in area than the original channel screen portions 140 and 142 were in the delivery screen mode. Additionally, the reallocation of space on screen 122 provides greater space for presenting information on the channel being adjusted or monitored.

Referring again to FIG. 5A, the medical device 14 includes dedicated or fixed tactile infuser buttons, and images of buttons on the LCD-touch screen 122. The fixed tactile buttons 133, 135, 137, and 139 provide the following functions: LOAD/EJECT button 133—opens and closes the cassette carriage; ON/OFF button 135—turns power on and off; ALARM SILENCE button 137—silences a silenceable alarm for a specified period of time, for example two minutes; and EMERGENCY STOP button 139—stops all channels. The LCD color touch screen 122 allows the user to access and use on-screen button images, for example 3D button images, and data entry fields. The touch screen 122 uses a membrane over the LCD display so a single keypress does not cause significant infusion pole movement nor is it mistaken for a double keypress. The touch screen also accommodates a keypress whether the user is wearing wet gloves, dry gloves, or no gloves.

LCD touch screen button images 143, 145, 147, and 149A-149E are located as shown in FIGS. 5A & 5B perform the following functions: Patient Information Tab 143—displays the clinical care area, preselected patient information (including without limitation name, ID number, etc.), and provides access to a more detailed patient information screen; Channel Level Therapy Buttons 145—accessed by button images on the infuser touch screen, are used to select an infusion therapy; Program Level Buttons 147—accessed by pressing areas, drop-down list triangles, boxes or text boxes on the programming screen, are used to select dose parameters of an infusion; and Device Level Buttons 149A-149E at the bottom of the touch screen are used to display and control device level features, including without limitation Mode 149A (for example, Operational or Biomed), Logs 149B, Locks 149C, Settings 149D, and Calculator display 149E. A wireless indicator image 102 displayed at the bottom of the screen 122 indicates that the medical device 14 is connected and ready for communication.

By using the Channel Level Therapy Buttons 145 and the Program Level Buttons 147, the healthcare practitioner can program each individual channel of the pump with specific fluid therapies in a variety of weight- and body surface area-based units such as micrograms/kg/hour, grams/m2/hr, and other delivery specifications for the following modes: Basic Therapy—includes dose calculation, which allows dose rate programming based on volume to be infused (VTBI), drug amount, infusion time and drug concentration and simple rate programming that allows programming of volumetric rate (ml/hr) based upon VTBI and time; Bolus delivery—allows user to program a single uninterrupted discrete delivery based on dose amount and time (the bolus can be delivered from the primary or a secondary container); Piggyback delivery—allows user to program the delivery of a secondary infusion, to be delivered through the same cassette as the primary infusion (the primary infusion is paused until the piggyback VTBI completes); and Advanced Programming. Advanced Programming mode provides various types of programs including: Multistep—which allows a sequential delivery of fluid in up to 10 steps, with fluid volumes and delivery rates programmable for each step based on Rate and Volume or Volume and Time; Variable Time—which allows up to 24 dose calculation steps at specified clock times; intermittent—a calculated dose or step to be delivered at regular intervals; and Taper—a delivery that ramps up and/or ramps down to a plateau rate.

Referring to FIGS. 4 & 5A, the graphical user interface 126 provides channel indicators presented on screen 122. The channel indicators associate on-screen programming, delivery, and alarm information with a particular delivery channel by using graphical depictions such as a channel indication icon 154, 155. The channel indication icon 154 or 155 is a graphical item clearly associating on-screen programming, delivery, and alarm information with a specified associated delivery channel. The channel indication icons 154 and 155 are located on a tab 158 associated with a specified delivery channel of the medical device The channel indication icon 154 or 155 may include but is not limited to a user readable letter or number, a machine-readable indicator 134, or a combination thereof. The graphical user interface program 126 also provides a drip indicator icon 160 and an infusion status icon 156 presented on screen 122.

Referring to FIG. 5B, the screen 122 provides an optional drop-down box 170 for setting an Allow Rate Catch-Up flag to one of an Enabled setting and a Disabled setting at the pump. The drop-down box 170 allows the user to enable or disable the rate catch-up function and to override the default rate catch-up flag provided in the drug library, if desired. When the Allow Rate Catch-Up flag is set to the Enabled setting, the user can enter a catch-up rate factor in the catch-up rate factor value box 172. In this example, the screen 122 also displays a catch-up rate factor limit value 174 and a catch-up rate factor alarm value 176 provided through the drug library. The catch-up rate factor limit value 174 is the maximum catch-up rate factor which the user can enter in the catch-up rate factor value box 172, i.e., the maximum catch-up rate factor or hard limit allowed for the particular therapeutic agent. The catch-up rate factor alarm value 176 is a soft limit on the catch-up rate factor. In one example, the screen 122 will provide an alarm when the user enters a value in the catch-up rate factor value box 172 which exceeds the catch-up rate factor alarm value 176, but the infusion pump will accept the catch-up rate factor after the user acknowledges the alarm or indicates a decision to override the soft limit as long as the catch-up rate factor does not exceed the hard limit or catch-up rate factor limit value 174. Those skilled in the art will appreciate that the catch-up rate factor limit value 174 and the catch-up rate factor alarm value 176 can be omitted or set to a high value as desired for a particular application. In one embodiment, the default values for the Allow Rate Catch-Up flag setting, catch-up rate factor value box 172, catch-up rate factor limit value 174, and/or catch-up rate factor alarm value 176 can be loaded into the infusion pump from a remote computer as part of a drug library editing program such as HOSPIRA MEDNET™ software. In another embodiment, the default values for the Allow Rate Catch-Up flag, catch-up rate factor value box 172, catch-up rate factor limit value 174, and/or catch-up rate factor alarm value 176 can be loaded into the infusion pump by the user at the infusion pump. In another hybrid embodiment, the default values can be established in a drug library downloaded to the pump and, if allowed by a setting in the drug library, later overridden or modified by the user at the pump. In another embodiment, the entire catch-up rate behavior can be predetermined by the manufacturer and hard coded into the pump, without any user customization being allowed.

Figure 6A:
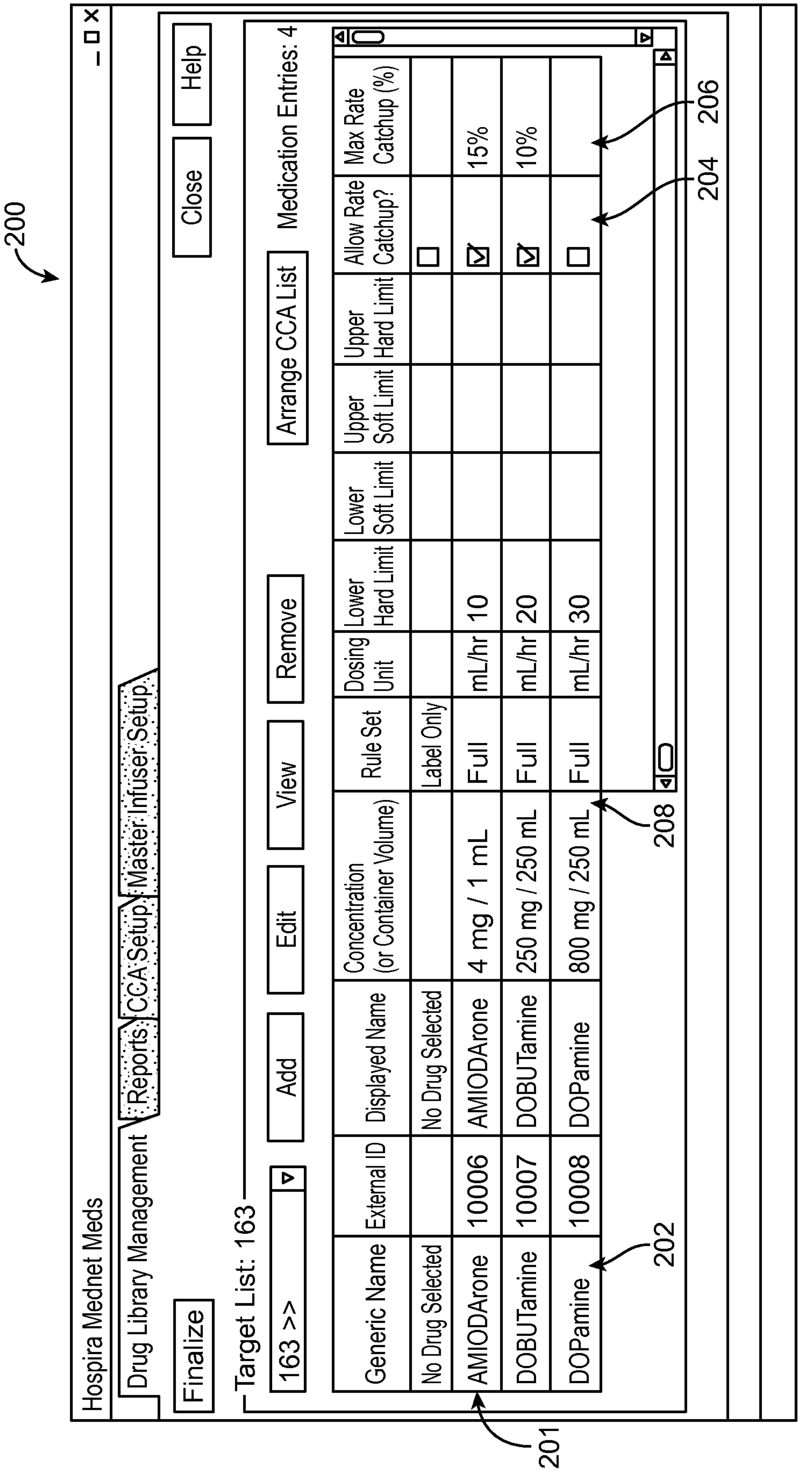
FIGS. 6A & 6B are screen shots of a graphical user interface and detail of the graphical user interface, respectively, for configuring a drug library, in accordance with the present invention.
Figure 6B:
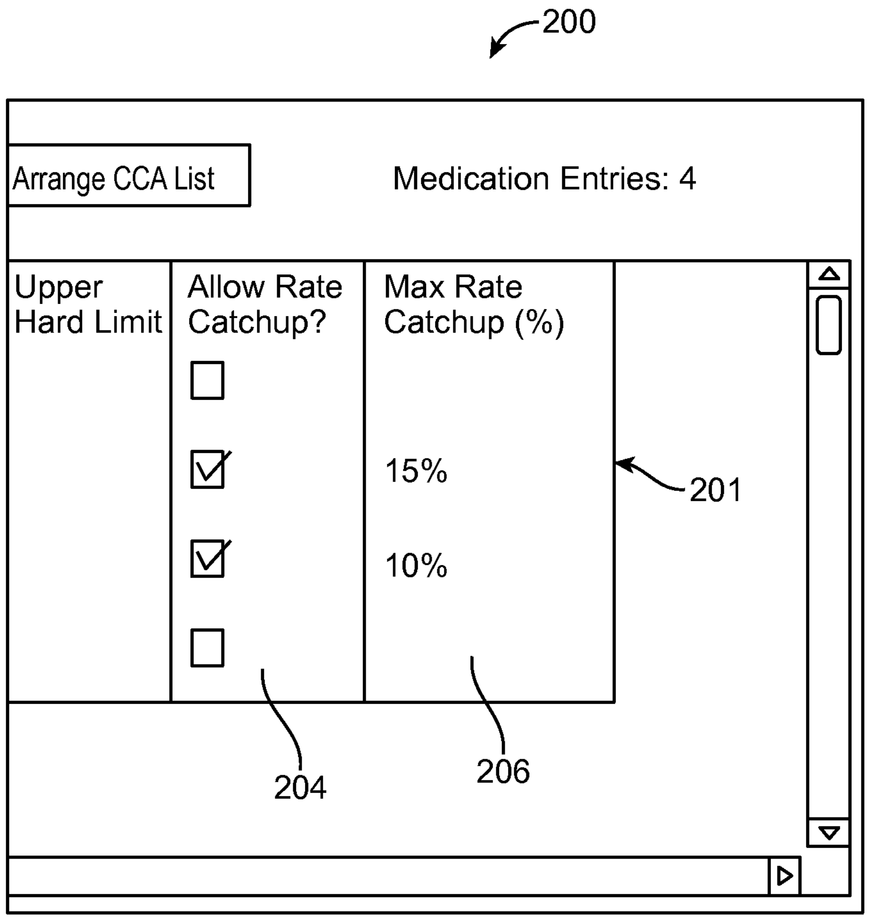

FIGS. 6A & 6B are screen shots of a graphical user interface and detail of the graphical user interface, respectively, for configuring a drug library, in accordance with the present invention. The graphical user interface 200 can be displayed on the display/input device 38 of the MMU 12 (as shown in FIG. 2) and used to receive data for creating or updating the drug library, such as the catch-up rate factor, Allow Rate Catch-up flag setting, maximum catch-up rate factor setting, maximum catch-up rate factor alarm setting, and the like.

Referring to FIGS. 6A & 6B, the graphical user interface 200 includes a table 201 to receive different drugs and therapeutic agents in the drug library database. Drug list 202 includes a list of the names of the drugs in the drug library, which could be the generic names, brand names or both. The drug list can include multiple entries for the same drug but different concentrations or clinical uses (cardiac, renal, pediatric). The Allow Rate Catch-Up Flag list 204 includes the allow rate catch-up flag setting for each drug/concentration/use entry ("drug entry" for short) in the drug list 202 to determine whether rate catch-up is allowed for the particular drug entry. In addition, the Allow Rate Catch-up flag setting can be a function of pump type and/or clinical care area location. The maximum rate catch-up list 206 includes the maximum catch-up rate factor setting for each drug entry in the drug list 202 for which rate catch-up is allowed. The maximum catch-up rate factor setting also can be a function of pump type and clinical care area location. In one embodiment, allowable maximum catch-up rate factors are regular linear percentages at predetermined intervals, e.g., 5%, 10%, 15%, 20%, et cetera. The table 201 can also include other parameters that constrain or limit the drug maximum catch-up rate such as the normal global constraints on rate already configured via the MMU 12 and HOSPIRA MEDNET™ software (Lower Hard Limit, Lower Soft Limit, Upper Soft Limit, and/or Upper Hard Limit). The maximum catch-up rate factor alarm setting and other drug maximum catch-up rate limits for each drug entry also can be a function of pump type and clinical care area location.

The catch-up rate factor is a simple percentage applied to the desired infusion rate to obtain a catch-up infusion rate when the actual accumulated infusion volume is less than the expected accumulated infusion volume. In some cases the desired infusion rate is input directly as a rate or volume per unit of time, such as ml/hr. In other cases the desired infusion rate is a calculated value based upon a dose and the weight or body surface area of the patient. For example, a dose of 10 ml/kg/hr can be prescribed for a patient who weighs 100 kg. Thus, the desired infusion rate would be calculated as 1000 ml/hr. In other cases the desired infusion rate is calculated based upon the dose and concentration of drug in the container. For example, if a dose of 10 mcg/hr is prescribed to be delivered from a 1000 ml container of fluid that has a concentration of 100 mcg of the drug, then the desired infusion rate is calculated at 100 ml/hr. There are other alternative dosing units that are known in the art to provide calculated desired infusion rates. In one embodiment, the catch-up rate factor is added to the desired infusion rate. In another embodiment, the catch-up rate factor (for example 1.05) is multiplied by the desired infusion rate. In one embodiment, allowable catch-up rate factors are regular linear percentages at predetermined intervals, e.g., 5%, 10%, 15%, 20%, et cetera to make it easier for the user to select a catch-up rate factor. The catch-up rate factor applies a linear adjustment to the desired infusion rate and does not rely on any input from physiological factors of the patient. Thus, the configurable closed loop delivery rate catch-up is straightforward and does not rely on complex algorithms or control schemes. Instead the feedback mechanism of this algorithm is based only on the measured versus expected accumulated volume delivered over time by the pump. The new rate Y is determined by a simple single order equation X+AX or AX; where A equals the catch-up rate factor as described above.

The Allow Rate Catch-up flag setting as a function of pump type can account for different pump types, makes and models, as well as uses for which various pump types are employed. In one example, one pump type using a cartridge and driving a plunger with a stepper motor can be used for general infusion such as saline solutions or the like, so that there is little risk in allowing rate catch-up. In another example, another pump type using a prefilled syringe can be used for analgesics or opiates, so that it may not be desirable to allow rate catch-up. Other pump types may have multiple uses or therapies and it may be desirable to control the enablement of the catch-up rate feature for each of the plurality of uses available with such a pump type.

The Allow Rate Catch-up flag setting can be a function of clinical care area location. In one example, an infusion pump used in a treatment area in which the patients are in serious or critical condition, such as an emergency or operating room, may not want to allow rate catch-up. In another example, an infusion pump used in a treatment area in which the patients are in good condition may want to allow rate catch-up.

Those skilled in the art will appreciate that the table 201 can also include other data as desired for a particular application. The table 201 can include other exemplary columns 208 for additional data for the different drugs, such as External Drug ID Numbers, Drug Display Names, Drug Concentration/Container Volume, Selected Drug Rule Set (Label Only, Limited, Full), Drug Dosing Unit, Drug Dosing Limits (Lower Hard Limit, Lower Soft/Alarm Limit, Upper Soft/Alarm Limit, and/or Upper Hard Limit) or the like.

The drug library provides flexibility for various combinations of parameters as desired for a particular application. The drug library can have different Allow Rate Catch-up flag settings for different drugs or drug entries in the drug library. The drug library can have different maximum permissible catch-up rate factor settings for different drugs in the drug library. The drug library can have a given drug listed in multiple different clinical care areas (CCAs) in the drug library with at least one of different Allow Rate Catch-up flag settings and different maximum catch-up rate factor settings for a the given drug.

Figure 7:
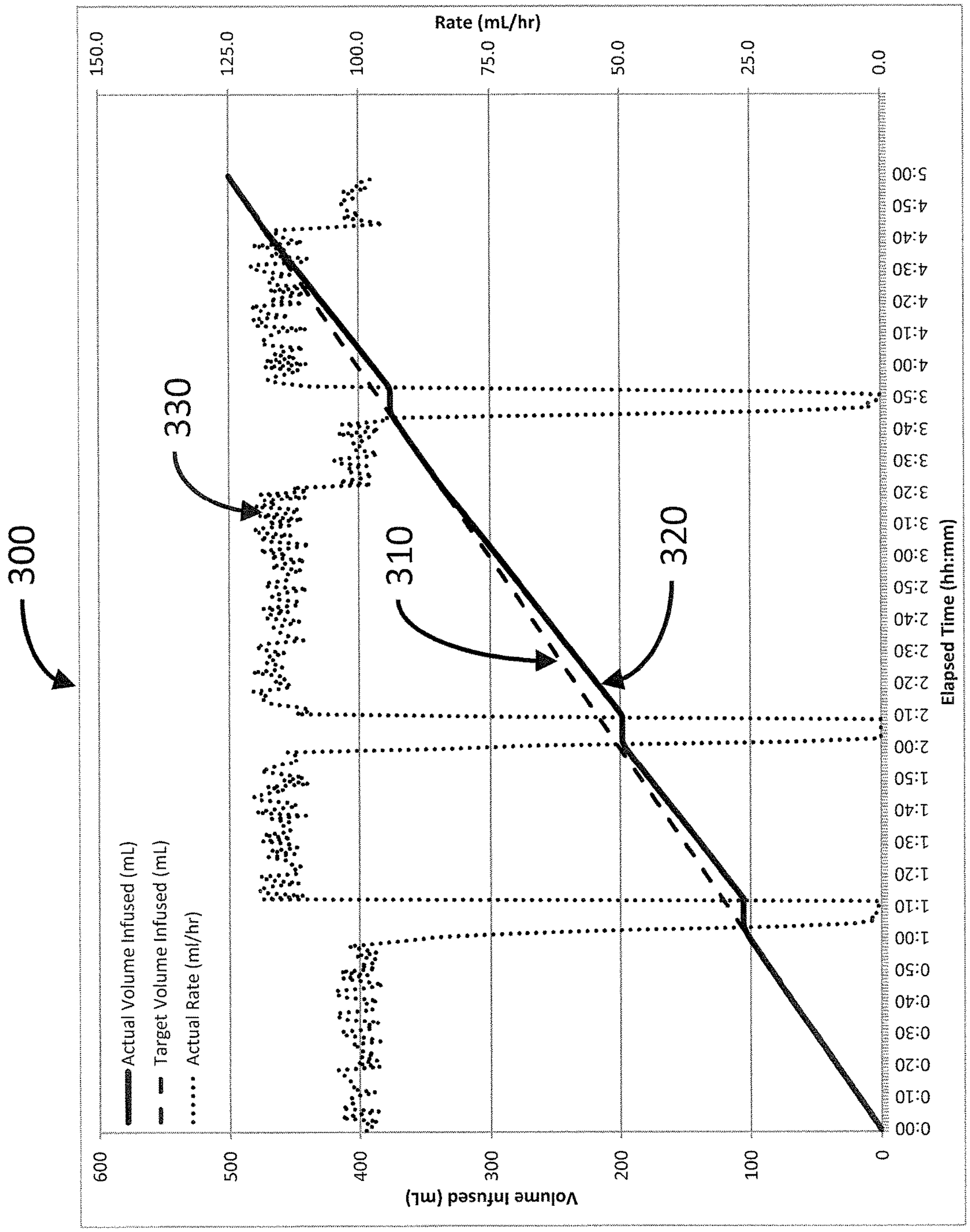
FIG. 7 is a graph of an infusion volume and infusion rate versus time modeled for an infusion with an infusion pump employing configurable closed loop delivery rate catch-up, in accordance with the present invention.

FIG. 7 is a graph of an infusion volume and infusion rate versus time modeled for an infusion with an infusion pump employing configurable closed loop delivery rate catch-up, in accordance with the present invention. The graph 300 includes the expected accumulated infusion volume 310, the actual accumulated infusion volume 320, and the infusion rate 330.

The expected accumulated infusion volume 310 increases linearly at a desired infusion rate of 100 ml per hour. The actual accumulated infusion volume 320 increases linearly from time 0:00 until time 1:00 at the originally programmed or desired infusion rate 330 of 100 ml per hour. At time 1:00, the infusion is interrupted so that the infusion rate 330 remains approximately zero and the actual accumulated infusion volume 320 remains about 100 ml until time 1:15, when the infusion resumes. At time 1:15, the actual accumulated infusion volume 320 is less than the expected accumulated infusion volume 310, so the infusion rate is increased by the catch-up rate factor of 15% and the infusion resumes at a catch-up infusion rate of 115 ml per hour from time 1:15 to time 2:00. At time 2:00, the actual accumulated infusion volume 320 has not quite yet caught up with the expected accumulated infusion volume 310 and the infusion is once again interrupted. The infusion rate 330 remains approximately zero and the actual accumulated infusion volume 320 remains about 200 ml until time 2:10, when the infusion resumes. From time 2:10 until time 3:20, the infusion is delivered at the catch-up infusion rate of 115 ml per hour until the actual accumulated infusion volume 320 equals the expected accumulated infusion volume 310 at time 3:20, when the infusion rate 330 is reduced to the originally programmed or desired infusion rate of 100 ml per hour. At time 3:45, the infusion is once again interrupted so that the infusion rate 330 remains approximately 0 and the actual accumulated infusion volume 320 remains at about 375 ml until the infusion resumes at time 3:55. From time 3:55 until time 4:40, the infusion is delivered at the catch-up infusion rate of 115 ml per hour until the actual accumulated infusion volume 320 equals the expected accumulated infusion volume 310 at time 4:40, when the infusion rate 330 is reduced to the originally programmed or desired infusion rate of 100 ml per hour. Thus, the desired accumulated volume of 500 ml has been delivered by the scheduled time 5:00 in spite of three interruptions in the infusion.

Figure 8:
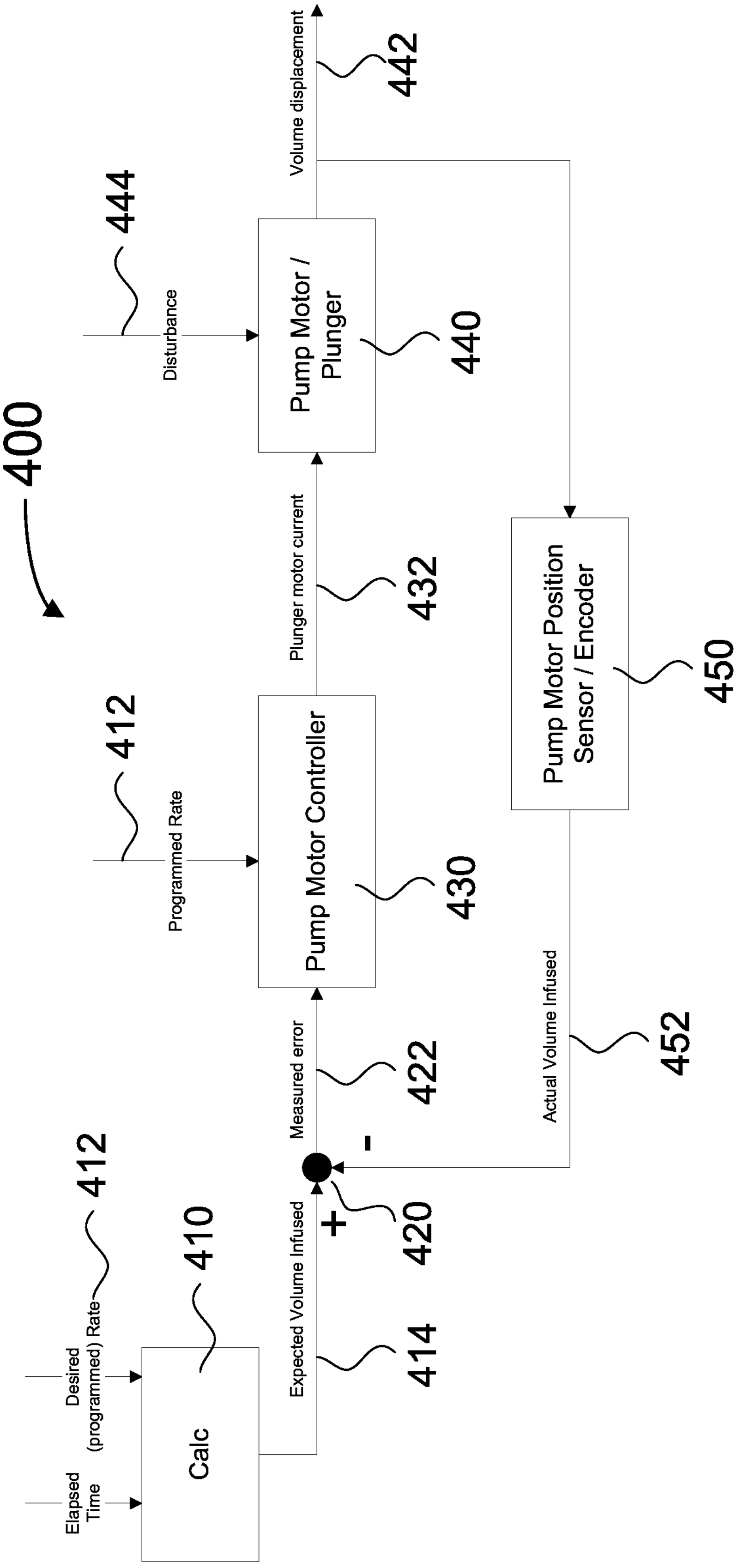
FIG. 8 is a block diagram of a control model for an infusion pump employing configurable closed loop delivery rate catch-up, in accordance with the present invention.

FIG. 8 is a block diagram of a control model for an infusion pump employing configurable closed loop delivery rate catch-up, in accordance with the present invention. The control model 400 includes an infusion volume calculator 410, a volume comparator 420, a pump controller 430, a pump drive 440, and a flow integrator 450. The infusion volume calculator 410 receives a desired infusion rate signal 412 and generates an expected accumulated infusion volume signal 414 from the originally programmed desired infusion rate signal 412 and the elapsed time. The volume comparator 420 receives the expected infusion volume signal 414 and an actual accumulated infusion volume signal 452, and generates a volume error signal 422 from the expected accumulated infusion volume signal 414 and the actual accumulated infusion volume signal 452. The pump controller 430 also receives the desired infusion rate signal 412 and the accumulated volume error signal 422, and generates a pump drive signal 432 from the desired infusion rate signal 412 and the accumulated volume error signal 422. The pump drive 440 receives the pump drive signal 432 to deliver the infusion 442. For modeling purposes, the pump drive 440 is subject to disturbances 444 which can cause or result in interrupted delivery of the infusion 442. The disturbance may include but are not limited to stoppages due to alarms, occlusions and other faults. The flow integrator 450 is operable to monitor the pump drive 440 and/or the infusion 442 and generate the actual accumulated infusion volume signal 452. In one embodiment, the pump drive 440 moves the plunger in a syringe and the flow integrator 450 senses pump drive/plunger position. In another embodiment, the pump drive 440 is a stepper motor and the flow integrator 450 counts pump strokes or motor steps. In yet another embodiment, the pump drive 440 is a rotary pump and the flow integrator 450 counts pump rotations. The present invention could also be applied with a drip counting device to provide the necessary feedback concerning the actual flow rate and/or accumulated volume. Returning to discussion of the embodiment for driven pumps, the pump drive signal 432 is a function of the desired infusion rate signal 412 multiplied by a catch-up rate factor when the volume error signal 422 meets (equals and/or exceeds) a threshold that indicates that actual accumulated infusion volume is less than expected accumulated infusion volume, to catch up interrupted delivery of an infusion. The pump drive signal 432 is a function of the desired infusion rate signal 412 alone or returns to the originally programmed or set rate when the accumulated volume error signal 422 indicates that the actual accumulated infusion volume is greater than or equal to the expected accumulated infusion volume.

Figure 9:
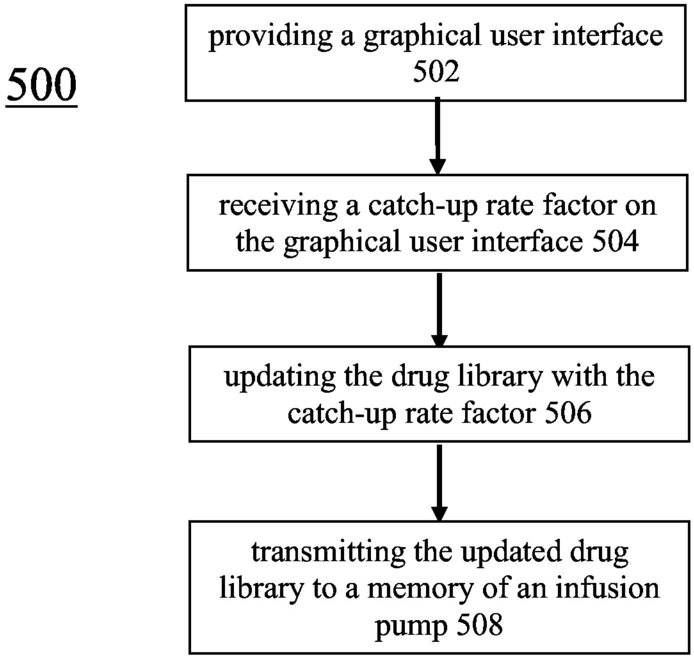
FIG. 9 is a flowchart of a method for configuring a drug library for use with an infusion system employing configurable closed loop delivery rate catch-up, in accordance with the present invention.

FIG. 9 is a flowchart of a method for configuring a drug library for use with an infusion system employing configurable closed loop delivery rate catch-up, in accordance with the present invention. The method 500 includes providing a graphical user interface 502 for modifying a drug library of the medication management unit; receiving a catch-up rate factor on the graphical user interface 504; updating the drug library with the catch-up rate factor 506; and transmitting the updated drug library to a memory of an infusion pump 508. The method 500 can be performed on a medication management unit having a processing unit and a storage medium coupled to the processing unit, the storage medium containing programming code executable by the processing unit to perform the steps of the method 500.

Those skilled in the art will appreciate that the drug library can include additional settings for a method for configuring a drug library for use with an infusion system employing configurable closed loop delivery rate catch-up as desired for a particular application. In one embodiment, the drug library can further include an Allow Rate Catch-up flag setting having one of an Enabled setting and a Disabled setting, the Allow Rate Catch-up flag setting being a function of a parameter selected from the group consisting of drug/concentration/use entry, pump type, and clinical care area location. In another embodiment, the drug library can further include a maximum catch-up rate factor setting having a numerical value, the maximum catch-up rate factor setting being a function of a parameter selected from the group consisting of drug entry, pump type and clinical care area location. In yet another embodiment, the drug library can further include a maximum catch-up rate factor alarm setting having a numerical value, the maximum catch-up rate factor alarm setting being a function of a parameter selected from the group consisting of drug entry, pump type and clinical care area location.

Figure 10:
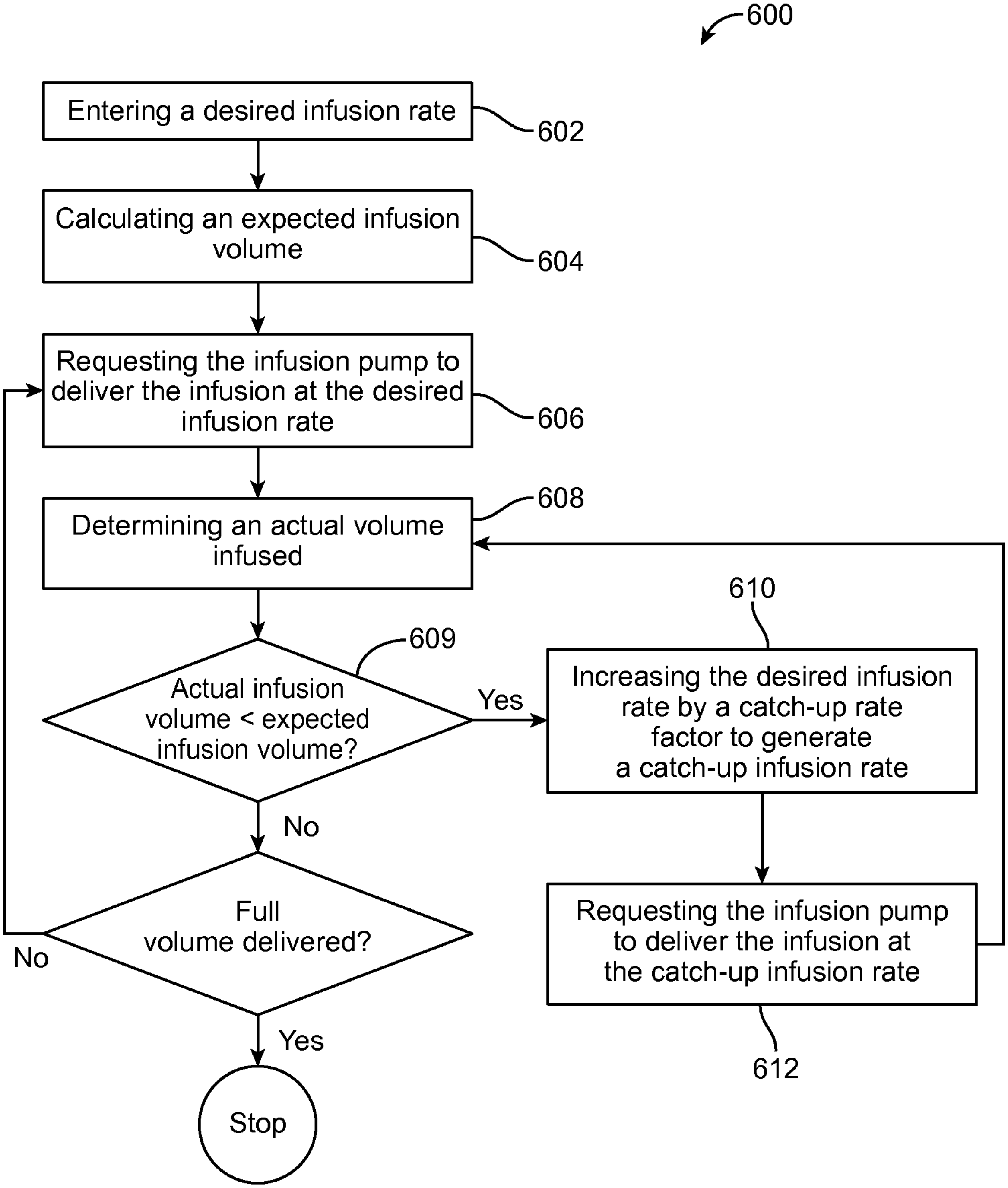
FIG. 10 is a flowchart of a method for operating an infusion pump employing configurable closed loop delivery rate catch-up, in accordance with the present invention.

FIG. 10 is a flowchart of a method for operating an infusion pump employing configurable closed loop delivery rate catch-up, in accordance with the present invention. The method 600 includes entering a desired infusion rate 602 for the infusion pump; calculating an expected accumulated infusion volume 604 as a function of time from the infusion rate; requesting the infusion pump to deliver the infusion at the desired infusion rate 606; determining an actual accumulated infusion volume 608 at a particular time; and determining whether the actual accumulated infusion volume is less than the expected accumulated infusion volume 609. When the actual accumulated infusion volume is less than the expected accumulated infusion volume, the method 600 continues with increasing the desired infusion rate by a catch-up rate factor to generate a catch-up infusion rate 610 and requesting the infusion pump to deliver the infusion at the catch-up infusion rate 612. When the actual accumulated infusion volume is not less than the expected accumulated infusion volume, the method 600 continues monitoring the output of the pump and with delivering the infusion at the originally programmed or desired infusion rate. The method 600 can also request the infusion pump to deliver the infusion at the originally programmed or desired infusion rate after delivery of the infusion at the catch-up infusion rate 612 when the actual accumulated infusion volume is equal to the expected accumulated infusion volume. Once the actual accumulated infusion volume is equal to or greater than the expected accumulated infusion volume, the method 600 continues by determining whether the full accumulated volume prescribed or programmed has been delivered or not. The method 600 stops if the full volume has been delivered, or loops back to continue with step 606 if more volume remains to be delivered.

The method 600 can also allow the user at the infusion pump to provide input. The method 600 can include a user at the infusion pump inputting an Allow Rate Catch-up flag setting to a Disabled setting to disable the increasing and the delivery rate catch-up function. The method 600 can include the user at the infusion pump inputting the catch-up rate factor to a desired value. In one embodiment, the catch-up rate factors are regular linear percentages at predetermined intervals, e.g., 5%, 10%, 15%, 20%, et cetera. In other embodiments, the drug library editor or the pump may allow the user more flexibility to customize the values and the intervals between them.

The method 600 may or may not require user action before applying the catch-up infusion rate if desired for a particular application. In one embodiment, the requesting the infusion pump to deliver the infusion at the catch-up infusion rate 612 can occur automatically, without user action, by increasing the desired infusion rate by a catch-up rate factor to generate a catch-up infusion rate 610. In another embodiment, the method 600 can include annunciating an alarm or warning before increasing the desired infusion rate by a catch-up rate factor to generate a catch-up infusion rate 610, and requiring the user acknowledge the alarm and confirm that the catch-up rate behavior is desired before the requesting the infusion pump to deliver the infusion at the catch-up infusion rate 612. In another embodiment, the method 600 can include annunciating an alarm or warning after increasing the desired infusion rate by a catch-up rate factor to generate a catch-up infusion rate 610, and allowing the user to confirm or reject the catch-up rate behavior. If the catch-up rate behavior is rejected, the infusion will revert to the originally programmed infusion rate.

The method 600 can also provide limits and alarms in response to user input. In one embodiment, the method 600 further includes rejecting the input catch-up rate factor when the desired value is greater than a maximum catch-up rate factor setting. In another embodiment, the method 600 further includes providing an alarm when the desired value is greater than a maximum catch-up rate factor alarm setting. In yet another embodiment, the increasing the desired infusion rate by a catch-up rate factor in the method 600 includes receiving an alarm when at the particular time the actual accumulated infusion volume is less than the expected accumulated infusion volume; and acknowledging the alarm prior to increasing the desired infusion rate by a catch-up rate factor to generate a catch-up infusion rate.

The method 600 can be performed on an infusion pump having a processor and the memory coupled to the processor, the memory containing programming code executable by the processor to perform the steps of the method 600. In one embodiment, the infusion pump 14 can be in electronic communication with a medication management unit 12 and the catch-up rate factor can be part of an updated drug library transmitted from the medication management unit 12 and received at the medical device 14.

Terms of equality and inequality (less than, greater than) as used herein as commonly used in the art, i.e., accounting for uncertainties present in measurement and control systems. Thus, such terms can be read as approximately equal, approximate less than, and/or approximately greater than. In one example, two values can be considered equal when they are within 5% of each other. In other aspects of the invention, an acceptable threshold of deviation or hysteresis can be established by the pump manufacturer, the editor of the drug library, or the user at the pump.

While the embodiments of the invention disclosed herein are presently considered to be preferred, various changes and modifications can be made without departing from the scope of the invention. The scope of the invention is indicated in the appended claims, and all changes that come within the meaning and range of equivalents are intended to be embraced therein.

What is claimed is:

1. An infusion system comprising one or more hardware processors configured to:

receive a desired infusion rate ("X") for an infusion pump;

calculate an expected accumulated infusion volume as a function of time from the desired infusion rate;

activate delivery of an infusion at the desired infusion rate;

determine an actual accumulated infusion volume at a particular time;

generate a catch-up infusion rate using the desired infusion rate and a catch-up rate factor, corresponding to an equation where the catch-up infusion rate=X*A based on a comparison of the actual accumulated infusion volume and the expected accumulated infusion volume; and change delivery of the infusion at the catch-up infusion rate, wherein the one or more hardware processors are further configured to receive input of a maximum permissible catch-up rate factor.

2. The infusion system of claim 1, wherein the one or more hardware processors are further configured to request the infusion pump to deliver the infusion at the desired infusion rate after delivery of the infusion at the catch-up infusion rate when the actual accumulated infusion volume is equal to the expected accumulated infusion volume.

3. The infusion system of claim 1, wherein the desired infusion rate is receiving from a drug library.

4. The infusion system of claim 3, wherein the one or more hardware processors are further configured to disable delivery at the catch-up infusion rate based on information received from the drug library.

5. The infusion system of claim 1, wherein the one or more hardware processors are further configured to disable delivery at the catch-up infusion rate based on a location of the infusion pump in a hospital.

6. The infusion pump of claim 1, wherein the one or more hardware processors are further configured to receive input of an Allow Rate Catch-up flag setting from a user at the infusion.

7. The infusion system of claim 1, wherein the generation of the catch-up infusion rate does not rely on physiological factors of a patient connected with the infusion pump.

8. The infusion system of claim 1, wherein the delivery of the infusion is changed to the catch-up infusion rate based on a location of the infusion pump.

9. The infusion system of claim 1, wherein the one or more hardware processors are configured to generate an alarm and request user input before changing the delivery of the infusion at the catch-up infusion rate.

10. An infusion method comprising:

receiving a desired infusion rate ("X") for an infusion pump;

calculating an expected accumulated infusion volume as a function of time from the desired infusion rate;

activating delivery of an infusion at the desired infusion rate;

determining an actual accumulated infusion volume at a particular time;

generating a catch-up infusion rate using the desired infusion rate and a catch-up rate factor, corresponding to an equation where the catch-up infusion rate=X*A based on a comparison of the actual accumulated infusion volume and the expected accumulated infusion volume; and changing delivery of the infusion at the catch-up infusion rate, and receiving an input of a maximum permissible catch-up rate factor.

11. The infusion method of claim 10, further comprising delivering the infusion at the desired infusion rate after delivery of the infusion at the catch-up infusion rate when the actual accumulated infusion volume is equal to the expected accumulated infusion volume.

12. The infusion method of claim 10, wherein the desired infusion rate is receiving from a drug library.

13. The infusion method of claim 12, further comprising disabling delivery at the catch-up infusion rate based on information received from the drug library.

14. The infusion method of claim 10, further comprising disabling delivery at the catch-up infusion rate based on a location in a hospital.

15. The infusion method of claim 10, further comprising receiving an input of an Allow Rate Catch-up flag setting from a user at the infusion.

16. The infusion method of claim 10, wherein the generation of the catch-up infusion rate does not rely on physiological factors of a patient.

17. The infusion method of claim 10, wherein the delivery of the infusion is changed to the catch-up infusion rate based on a location of the infusion pump.

18. The infusion method of claim 10, further comprising generating an alarm and request user input before changing the delivery of the infusion at the catch-up infusion rate.

19. An infusion system comprising one or more hardware processors configured to:

receive a desired infusion rate ("X") for an infusion pump;

calculate an expected accumulated infusion volume as a function of time from the desired infusion rate;

activate delivery of an infusion at the desired infusion rate;

determine an actual accumulated infusion volume at a particular time;

generate a catch-up infusion rate using the desired infusion rate and a catch-up rate factor, corresponding to an equation where the catch-up infusion rate=X*A based on a comparison of the actual accumulated infusion volume and the expected accumulated infusion volume;

change delivery of the infusion at the catch-up infusion rate; and disable delivery at the catch-up infusion rate based on a location of the infusion pump in a hospital.

20. An infusion system comprising one or more hardware processors configured to:

receive a desired infusion rate ("X") for an infusion pump;

calculate an expected accumulated infusion volume as a function of time from the desired infusion rate;

activate delivery of an infusion at the desired infusion rate;

determine an actual accumulated infusion volume at a particular time;

generate a catch-up infusion rate using the desired infusion rate and a catch-up rate factor, corresponding to an equation where the catch-up infusion rate=X*A based on a comparison of the actual accumulated infusion volume and the expected accumulated infusion volume; and change delivery of the infusion at the catch-up infusion rate, wherein the delivery of the infusion is changed to the catch-up infusion rate based on a location of the infusion pump.

* * * * *